(12) United States Patent
Xu

(10) Patent No.: US 8,822,465 B2
(45) Date of Patent: Sep. 2, 2014

(54) QUINOLINE COMPOUND COMPOSING 1,2,4-TRIAZINE-DIONE AND USE THEREOF

(71) Applicant: Hua Xu, Wuhan (CN)

(72) Inventor: Hua Xu, Wuhan (CN)

(73) Assignee: Wuhan Shengyun Biopharma Co., Ltd., Wuchang District, Wuhan (CN)

( * ) Notice: Subject to any disclaimer, the term of this patent is extended or adjusted under 35 U.S.C. 154(b) by 0 days.

(21) Appl. No.: 13/828,615

(22) Filed: Mar. 14, 2013

(65) Prior Publication Data

US 2013/0252958 A1 Sep. 26, 2013

(30) Foreign Application Priority Data

Mar. 26, 2012 (CN) .......................... 2012 1 0080827

(51) Int. Cl.
*A61K 31/5377* (2006.01)
*A61K 31/53* (2006.01)
*C07D 401/14* (2006.01)
*C07D 401/12* (2006.01)

(52) U.S. Cl.
CPC ............ *C07D 401/14* (2013.01); *C07D 401/12* (2013.01)
USPC ......... 514/236.2; 514/242; 544/182; 544/112

(58) Field of Classification Search
USPC ................. 514/236.2, 242; 544/182, 112
See application file for complete search history.

(56) References Cited

U.S. PATENT DOCUMENTS

2005/0037431 A1 2/2005 Kirchhofer et al.

FOREIGN PATENT DOCUMENTS

CN 200780029441.2 9/2009

*Primary Examiner* — Kristin Vajda
(74) *Attorney, Agent, or Firm* — Juan Carlos A. Marquez; Morris, Manning & Martin, LLP

(57) ABSTRACT

The present invention relates to a quinoline derivative represented by general formula (I) or a pharmaceutically acceptable salt, hydrate, solvate or prodrug thereof, wherein Ar, $R_1$, $R_2$, $R_3$, X, Y and n have the meanings given in the description. The present invention also relates to the comparatively strong effect of the compound represented by general formula (I) on inhibiting c-Met kinase. The present invention further relates to the use of this compound or a pharmaceutically acceptable salt, hydrate, solvate or prodrug thereof in the manufacturing of a medicament for treating the disease caused by abnormally over-expressing c-Met kinase, in particular, for treating or preventing cancer.

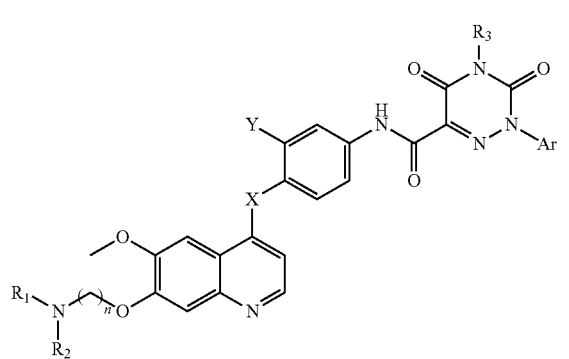

13 Claims, No Drawings

QUINOLINE COMPOUND COMPOSING 1,2,4-TRIAZINE-DIONE AND USE THEREOF

TECHNICAL FIELD

The present invention relates to a new quinoline compound comprising 1,2,4-triazine-3,5-dione and a pharmaceutically acceptable salt, hydrate, solvate or prodrug thereof, a preparation method therefore and a pharmaceutical composition containing the same. The present invention also relates to the comparatively strong effect of the quinoline compound comprising 1,2,4-triazine-3,5-dione on inhibiting c-Met kinase. The present invention further relates to the use of this compound or a pharmaceutically acceptable salt, hydrate, solvate or prodrug thereof in the manufacturing of a medicament for treating the disease caused by abnormally over-expressing c-Met kinase, in particular, for treating or preventing cancer.

BACKGROUND ART

Hepatocyte growth factor (HGF) is a powerful mitogen which stimulates the hepatocyte proliferation. The single receptor for HGF, c-Met, is a transmembrane protein encoded by proto-oncogene c-Met. HGF activates c-Met, which results in the cascade activation by the signal transduction pathway, such as ras/mitogen-activated protein (MAP) kinase pathway, and phosphatidylinositol 3-kinase/protein kinase B pathway. A series of biological effects, such as scattering, cell movement, invasion, cell migration and eventual metastasis, occur in cells.

The human HGF gene is located on the long arm of chromosome 7 (7q21.1), has about 70 kb, and comprises 18 extrons and 17 introns. HGF is produced mainly from interstitial cells. The mature HGF has a molecular weight of $9.0 \times 10^4$. An alpha chain of $6.0 \times 10^4$ and a beta chain of $3.0 \times 10^4$ are connected by a disulfide linkage to form a heterodimer. The alpha chain is in a short hairpin structure and has an N-terminal region in which 4 Kringle domains are connected. The hairpin structure in the N-terminal region and the structure of its first two Kringle domains are essential for HGF to perform its biological effect. The beta chain has a serine protease-like structure, but has no catalytic activity of the protease. However, the beta chain is a prerequisite for HGF to perform its biological activity.

The human c-Met gene is located on the long arm of chromosome 7 (7q31), has about 110 kb, and comprises 21 extrons. In a mature c-Met, an alpha subunit of $5.0 \times 10^4$ and a beta subunit of $1.4 \times 10^5$ form a heterodimer. The alpha subunit is located on the exocellular part. The beta subunit includes the exocellular region, the transmembrane region and the intracellular region. The alpha subunit and the exocellular region of the beta subunit serve as the ligand recognition site and incorporate HGF. The intracellular region has a tyrosine kinase activity, and is a site where several signaling molecules, interact.

The HGF/c-Met signal transducting path is widely present in a variety of cells, and has a significant physiological adjustment effect on the growth and development of tissues and organs. However, the over-expression of HGF or c-Met in cells generally results in the invasion and metabasis of tumor cells.

The HGF/c-Met signal system is closely relevant to the invasion and metabasis of tumor cells. When stably transfecting cDNA of HGF to low metastatic cell line SMMC and comparing the cell growth and the cell mobility before and after the transfection, the results show that the high expression of HGF in the hepatoma carcinoma cells can promote the growth, invasion and metabasis of hepatoma carcinoma cells. It is found by Miura, et al. that the invasion of hepatoma carcinoma cell line AH109A is mediated by the paracrine secretion and autocrine of HGF. In the poorly differentiated tumors and the recurrent patients having the early primary hepatocellular carcinoma, c-Met is in an over-expression.

The down-regulation or the abnormal regulation of Met and/or HGF, the over-expression of Met and the mutation of Met are all relevant to the uncontrolled cell proliferation and survival. These factors occur in the early stage of tumors and play a key role in the invasion, growth and metabasis of tumor cells. The over-expression of Met and HGF are relevant to poor prognosis and diagnosis. Up to now, much evidence demonstrates that HGF is acting as a regulator in the cancer occurrence, invasion and metabasis. In the mouse model of tumor xenograft, inhibition of Met results in the tumor growth slowdown, which is because the specific antibody of c-Met has been expressed to block the combination of HGF and c-Met. Moreover, c-Met is also over-expressed in the cells of nonsmall-cell lung cancer and small-cell lung cancer, lung cancer, breast cancer, colon cancer and prostatic carcinoma. Since c-Met appears to play an important role in tumor formation of several tumors, several inhibition strategies have been applied to therapeutically target the receptor tyrosine kinase, which also makes Met the important target in the development of anticancer drugs.

Modulation of the HGF/c-met signaling pathway may be effected by regulating binding of HGF beta chain to c-Met. In particular embodiments, the zymogen-like form of HGF beta mutant was shown to bind c-Met with 14-fold lower affinity than the wild-type serine protease-like form, suggesting that optimal interactions result from conformational changes upon cleavage of the single-chain form (US 2005/0037431). Extensive mutagenesis of the HGF beta region corresponding to the active site and activation domain of serine proteases showed that 17 of the 38 purified two-chain HGF mutants resulted in impaired cell migration or c-Met phosphorylation, without loss in Met binding. However, the reduced biological activities were well correlated with reduced Met binding of corresponding mutants of HGF beta itself in assays eliminating dominant alpha-chain binding contributions (CN200780029441.2).

Based on the relevant prior art references, the present inventors design and synthesize a series of quinoline deravatives comprising 1,2,4-triazine-3,5-dione. By an in-vitro activity screen, it is shown that this series of compounds have an anti-tumor activity.

CONTENTS OF INVENTION

The present invention relates to a quinoline compound comprising 1,2,4-triazine-3,5-dione represented by general formula (I) or a pharmaceutically acceptable salt, hydrate, solvate or prodrug thereof,

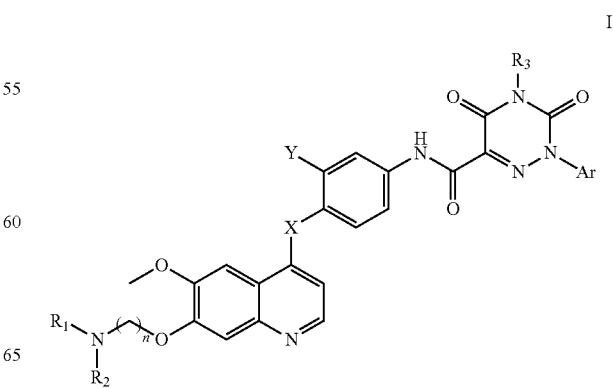

wherein,

X is O, S, NH, NCH$_3$;

Y is H, halogen;

n is an integral between 2 and 6;

$R_1$ and $R_2$ are identical or different, and independently and respectively selected from the group consisting of hydrogen, $C_1$-$C_{10}$alkyl, $C_3$-$C_7$cycloalkyl, $C_2$-$C_{10}$alkenyl and $C_2$-$C_{10}$alkynyl, which can be optionally substituted by 1-3 identical or different $R_4$ substituents; or $R_1$ and $R_2$ together with the nitrogen atom bonded thereto form 5-10 membered heterocyclyl or 5-10 membered heteroaryl, said heterocyclyl and heteroaryl optionally contain 1-4 hetero atoms selected from N, O and S besides the nitrogen atom bonded to $R_1$ and $R_2$, said heterocyclyl optionally comprises 1 or 2 carbon-carbon double bonds besides the nitrogen atom bonded to $R_1$ and $R_2$, said heterocyclyl and heteroaryl are optionally substituted by 1-3 identical or different $R_4$ substituents;

$R_4$ is $C_1$-$C_6$alkyl, hydroxy, cyano, carboxyl, an ester group;

$R_3$ is H, $C_1$-$C_4$alkyl, $C_3$-$C_6$cycloalkyl, allyl, —CH$_2$—Ar$_1$;

Ar$_1$ is phenyl, and optionally substituted by 1-3 identical or different $R_5$ substituents;

Ar is $C_6$-$C_{10}$aryl, 5-10 membered heteroaryl, wherein said heteroaryl contains 1-3 hetero atoms selected from N, O and S, and Ar is optionally substituted by 1-3 identical or different $R_5$ substituents;

$R_5$ is hydroxy, halogen, nitro, amino, cyano, ($C_1$-$C_6$)alkyl, ($C_1$-$C_6$)alkenyl, ($C_1$-$C_6$)alkynyl, ($C_1$-$C_6$)alkoxyl, ($C_1$-$C_6$) alkyl or ($C_1$-$C_6$)alkoxyl optionally substituted by hydroxy, amino or halogen, mono or di[($C_1$-$C_6$)alkyl] substituted amino, ($C_1$-$C_6$)alkylamido, a carboxyl radical which is free, salified, esterified or amidated, ($C_1$-$C_6$)alkylsulfinyl, sulfonyl, ($C_1$-$C_6$)alkoxyl, ($C_1$-$C_6$)alkyl, ($C_1$-$C_6$)alkylacyl, carbamoyl, mono or di($C_1$-$C_6$alkyl) substituted carbamoyl, ($C_1$-$C_3$)alkylenedioxy.

The present invention preferably relates to a quinoline compound comprising 1,2,4-triazine-3,5-dione represented by general formula (I) or a pharmaceutically acceptable salt, hydrate, solvate or prodrug thereof, wherein, X is O, S;

Y is halogen;

n is an integral between 2 and 6;

$R_1$ and $R_2$ are identical or different, and independently and respectively selected from the group consisting of hydrogen, $C_1$-$C_6$alkyl, $C_3$-$C_6$cycloalkyl, which can be optionally substituted by 1-3 identical or different $R_4$ substituents;

or $R_1$ and $R_2$ together with the nitrogen atom bonded thereto form 5-10 membered heterocyclyl, said heterocyclyl optionally contains 1-4 hetero atoms selected from N, O and S besides the nitrogen atom bonded to $R_1$ and $R_2$, said heterocyclyl optionally comprises 1 or 2 carbon-carbon double bonds or triple bonds besides the nitrogen atom bonded to $R_1$ and $R_2$, said heterocyclyl is optionally substituted by 1-3 identical or different $R_4$ substituents.

$R_4$ is $C_1$-$C_4$alkyl, $C_1$-$C_4$alkoxyl, halo, hydroxy, cyano, carboxyl, an ester group;

$R_3$ is H, $C_1$-$C_4$alkyl, $C_3$-$C_6$cycloalkyl, allyl, benzyl;

Ar is $C_6$-$C_{10}$aryl, 5-10 membered heteroaryl, wherein said heteroaryl contains 1-3 hetero atoms selected from N, O and S, and Ar is optionally substituted by 1-3 identical or different $R_5$ substituents;

$R_5$ is hydroxy, halogen, nitro, amino, cyano, ($C_1$-$C_6$)alkyl, ($C_1$-$C_6$)alkenyl, ($C_1$-$C_6$)alkynyl, ($C_1$-$C_6$)alkoxyl, ($C_1$-$C_6$) alkyl or ($C_1$-$C_6$)alkoxyl optionally substituted by hydroxy, amino or halogen, mono or di[($C_1$-$C_6$)alkyl] substituted amino, ($C_1$-$C_6$)alkylamido, a carboxyl radical which is free, salified, esterified or amidated, ($C_1$-$C_6$)alkylsulfinyl, sulfonyl, ($C_1$-$C_6$)alkoxyl, ($C_1$-$C_6$)alkyl, ($C_1$-$C_6$)alkylacyl, carbamoyl, mono or di($C_1$-$C_6$alkyl) substituted carbamoyl, ($C_1$-$C_3$)alkylenedioxy.

Furthermore, the present invention preferably relates to a quinoline compound comprising 1,2,4-triazine-3,5-dione represented by general formula (I) or a pharmaceutically acceptable salt, hydrate, solvate or prodrug thereof, wherein, X is O;

Y is H, F;

n is an integral between 2 and 4;

$R_1$ and $R_2$ together with the nitrogen atom bonded thereto form 5-6 membered heterocyclyl, said heterocyclyl optionally contains 1-3 hetero atoms selected from N, O and S besides the nitrogen atom bonded to $R_1$ and $R_2$, said heterocyclyl optionally comprises 1 or 2 carbon-carbon double bonds or triple bonds besides the nitrogen atom bonded to $R_1$ and $R_2$, said heterocyclyl is optionally substituted by 1-3 identical or different $R_4$ substituents;

$R_4$ is $C_1$-$C_4$alkyl, $C_1$-$C_4$alkoxyl, halo, hydroxy, cyano, carboxyl, an ester group;

$R_3$ is H, $C_1$-$C_4$alkyl, allyl, benzyl;

Ar is phenyl, 5-6 membered heteroaryl, wherein said heteroaryl contains 1-3 hetero atoms selected from N, O and S, and Ar is optionally substituted by 1-3 identical or different $R_5$ substituents;

$R_5$ is hydroxy, halogen, nitro, amino, cyano, ($C_1$-$C_6$)alkyl, ($C_1$-$C_6$)alkenyl, ($C_1$-$C_6$)alkynyl, ($C_1$-$C_6$)alkoxyl, ($C_1$-$C_6$) alkyl or ($C_1$-$C_6$)alkoxyl optionally substituted by hydroxy, amino or halogen, mono or di[($C_1$-$C_6$)alkyl] substituted amino, ($C_1$-$C_6$)alkylamido, a carboxyl radical which is free, salified, esterified or amidated, ($C_1$-$C_6$)alkylsulfinyl, sulfonyl, ($C_1$-$C_6$)alkoxyl, ($C_1$-$C_6$)alkyl, ($C_1$-$C_6$)alkylacyl, carbamoyl, mono or di($C_1$-$C_6$alkyl) substituted carbamoyl, ($C_1$-$C_3$)alkylenedioxy.

The present invention particularly preferably relates to a quinoline compound comprising 1,2,4-triazine-3,5-dione represented by general formula (I) or a pharmaceutically acceptable salt, hydrate, solvate or prodrug thereof, wherein, X is O;

Y is F;

n is an integral between 2 and 4, preferably 3;

$R_1$ and $R_2$ together with the nitrogen atom bonded thereto form 5-6 membered saturated heterocyclyl, said saturated heterocyclyl optionally contains one hetero atom selected from N, O and S besides the nitrogen atom bonded to $R_1$ and $R_2$, and is optionally substituted by 1-3 identical or different $R_4$ substituents; particularly preferably $R_1$ and $R_2$ together with the nitrogen atom bonded thereto form 1-piperidinyl, 4-morpholinyl, 4-methyl-1-piperazinyl, 1-piperazinyl, 4-methyl-1-piperidinyl, 1-pyrrolidyl, 4-thiomorpholinyl;

$R_4$ is $C_1$-$C_4$alkyl;

$R_3$ is hydrogen, $C_1$-$C_4$alkyl, preferably methyl, ethyl, propyl, butyl and allyl; more preferably methyl Ar is phenyl, pyridinyl, pyrrolyl, furyl, thienyl, preferably phenyl, and Ar is optionally substituted by 1-3 identical or different $R_5$ substituents.

$R_5$ is hydroxy, halogen, nitro, amino, cyano, ($C_1$-$C_6$)alkyl, ($C_1$-$C_6$)alkenyl, ($C_1$-$C_6$)alkynyl, ($C_1$-$C_6$)alkoxyl, ($C_1$-$C_6$) alkyl or ($C_1$-$C_6$)alkoxyl optionally substituted by hydroxy, amino or halogen, mono or di[($C_1$-$C_6$)alkyl] substituted amino, ($C_1$-$C_6$)alkylamido, a carboxyl radical which is free, salified, esterified or amidated, ($C_1$-$C_6$)alkylsulfinyl, sulfonyl, ($C_1$-$C_6$)alkoxyl, ($C_1$-$C_6$)alkyl, ($C_1$-$C_6$)alkylacyl, carbamoyl, mono or di($C_1$-$C_6$alkyl) substituted carbamoyl, ($C_1$-$C_3$)alkylenedioxy;

$R_5$ is preferably halogen, $(C_1-C_4)$alkyl, $(C_1-C_4)$alkoxyl, $(C_1-C_4)$alkyl or $(C_1-C_4)$alkoxyl optionally substituted by halogen, mono or di($C_1-C_6$alkyl) substituted amino, $(C_1-C_4)$alkoxyl($C_1-C_4$)alkyl, $(C_1-C_6)$alkylacyl, carbamoyl, mono or di($C_1-C_6$alkyl) substituted carbamoyl, $(C_1-C_3)$alkylenedioxy.

$R_5$ is more preferably halogen, methyl, ethyl, methoxy, ethoxy, trifluoromethyl and trifluoromethoxy; $R_5$ is particularly preferably fluoro, chloro, trifluoromethyl and methyl.

The present compound of general formula (I) or a pharmaceutically acceptable salt, hydrate, solvate or prodrug thereof is more preferably selected from the group consisting of the following compounds, which however do not imply any limitation to the scope of the present invention:

N-[3-fluoro-4-[6-methoxy-7-[3-(4-morpholinyl)propyloxy]quinolin-4-oxy]phenyl]-2-phenyl-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-phenyl-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-phenyl-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-phenyl-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-phenyl-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-4-methyl-3,5-dicarbonyl-2-(3-trifluoromethylphenyl)-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(4-morpholinyl)propyloxy)quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(morpholin-1-yl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-phenyl-4-butyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-phenyl-4-butyl-3,5-dioxo-2,3,4,5-tetrahydro-1,2,4-triazine-6-carboxamide;

N-[3-fluoro-4-[7-methoxy-6-[3-(4-methyl-1-piperazinyl)propyloxy]quinolin-4-oxy]phenyl]-2-phenyl-4-butyl-3,5-dioxo-2,3,4,5-tetrahydro-1,2,4-triazine-6-carboxamide;

N-[3-fluoro-4-[7-methoxy-6-[3-(4-methyl-1-piperidinyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(4-methyl-1-piperazinyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(4-methyl-1-piperazinyl)propyloxy]quinolin-4-oxy]phenyl]-2-(4-chlorophenyl)-4-allyl-3,5-dioxo-2,3,4,5-tetrahydro-1,2,4-triazine-6-carboxamide;

N-[3-fluoro-4-[7-methoxy-6-[3-(4-methyl-1-piperidinyl)propyloxy]quinolin-4-oxy]phenyl]-2-(4-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-trifluoromethylphenyl)-4-allyl-3,5-dioxo-2,3,4,5-tetrahydro-1,2,4-triazine-6-carboxamide;

N-[3-fluoro-4-[7-methoxy-6-[3-(1-piperidinyl)propyloxy]quinolin-4-oxy]phenyl]-2-(2-trifluoromethylphenyl)-4-allyl-3,5-dioxo-2,3,4,5-tetrahydro-1,2,4-triazine-6-carboxamide;

N-[3-fluoro-4-[7-methoxy-6-[3-(1-piperidinyl)propyloxy]quinolin-4-oxy]phenyl]-2-phenyl-4-allyl-3,5-dioxo-2,3,4,5-tetrahydro-1,2,4-triazine-6-carboxamide;

N-[3-fluoro-4-[7-methoxy-6-[3-(4-methyl-1-piperidinyl)propyloxy]quinolin-4-oxy]phenyl]-2-(4-chlorophenyl)-4-allyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-(2-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(3-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-methylphenyl)-4-allyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(4-morpholinyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(1-piperidinyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(4-morpholinyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(1-piperidinyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(1-piperidinyl)propyloxy]quinolin]-4-oxy]phenyl]-2-(3-trifluoromethylphenyl)-4-benzyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin]-4-oxy]phenyl]-2-(3-trifluoromethylphenyl)-4-benzyl-3,5-dioxo-2,3,4,5-tetrahydro-1,2,4-triazine-6-carboxamide;

The following synthesis schemes will illustrate the preparation of the present compounds of general formula (I) of the present invention, wherein all starting materials can be prepared by the methods depicted in the schemes or the methods well known to one of ordinary skill in the organic chemistry art, or are commercially available. All of the final compounds of the present invention are prepared by the methods depicted in the schemes or similar methods, and these methods are well known to one of ordinary skill in the organic chemistry art. All variable factors as involved in these schemes are defined as follows or defined as in claims. The present compounds of general formula (I) of the present invention can be prepared according to the method in Scheme 1 by the substitution reaction from Intermediates A and C, wherein the variants $R_1$, $R_2$, n, X, Y, $R_3$ and $R_5$ are defined as in the claims.

Scheme 1

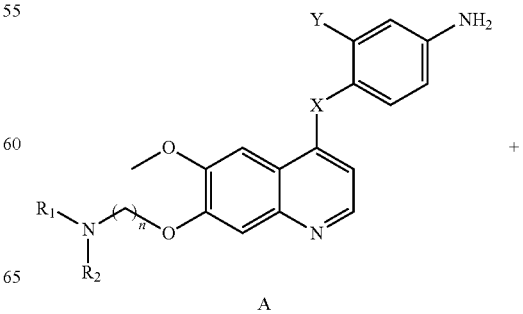

A

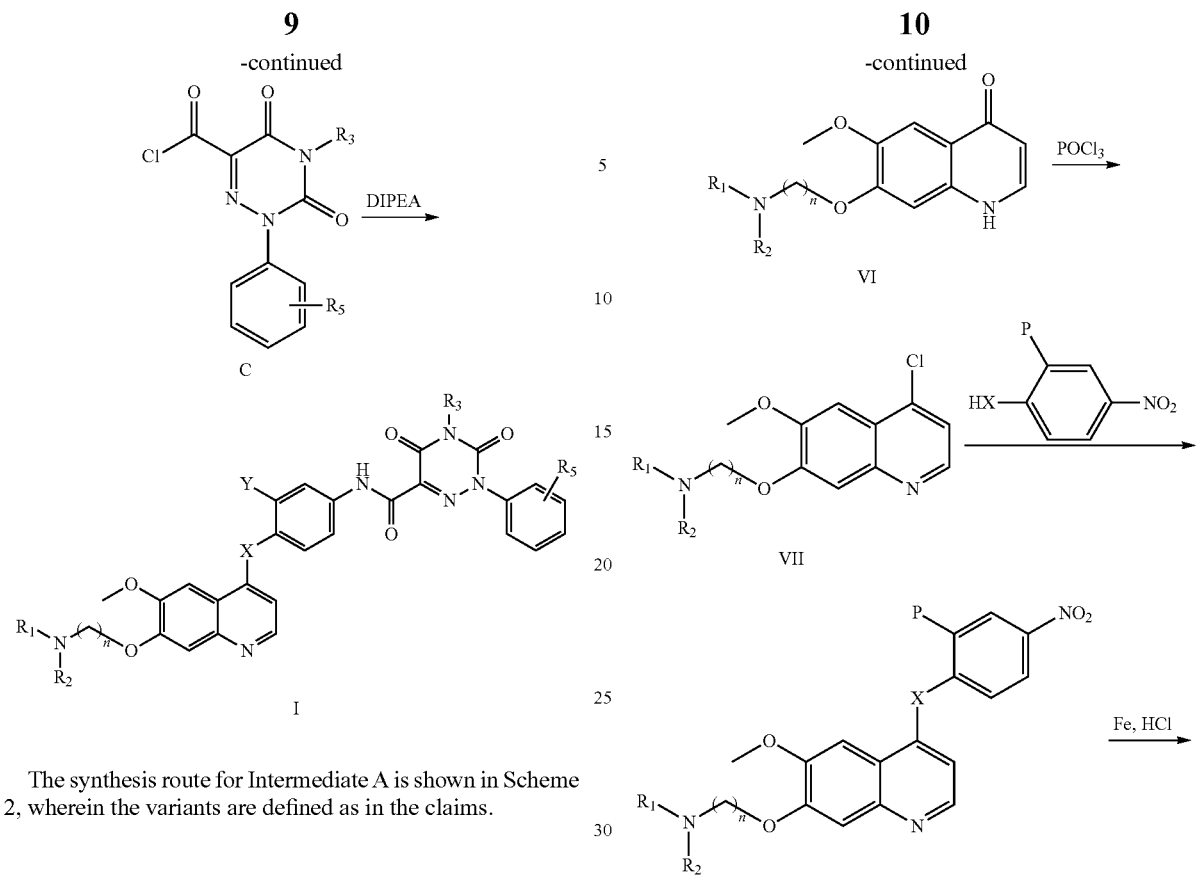
The synthesis route for Intermediate A is shown in Scheme 2, wherein the variants are defined as in the claims.
Scheme 2
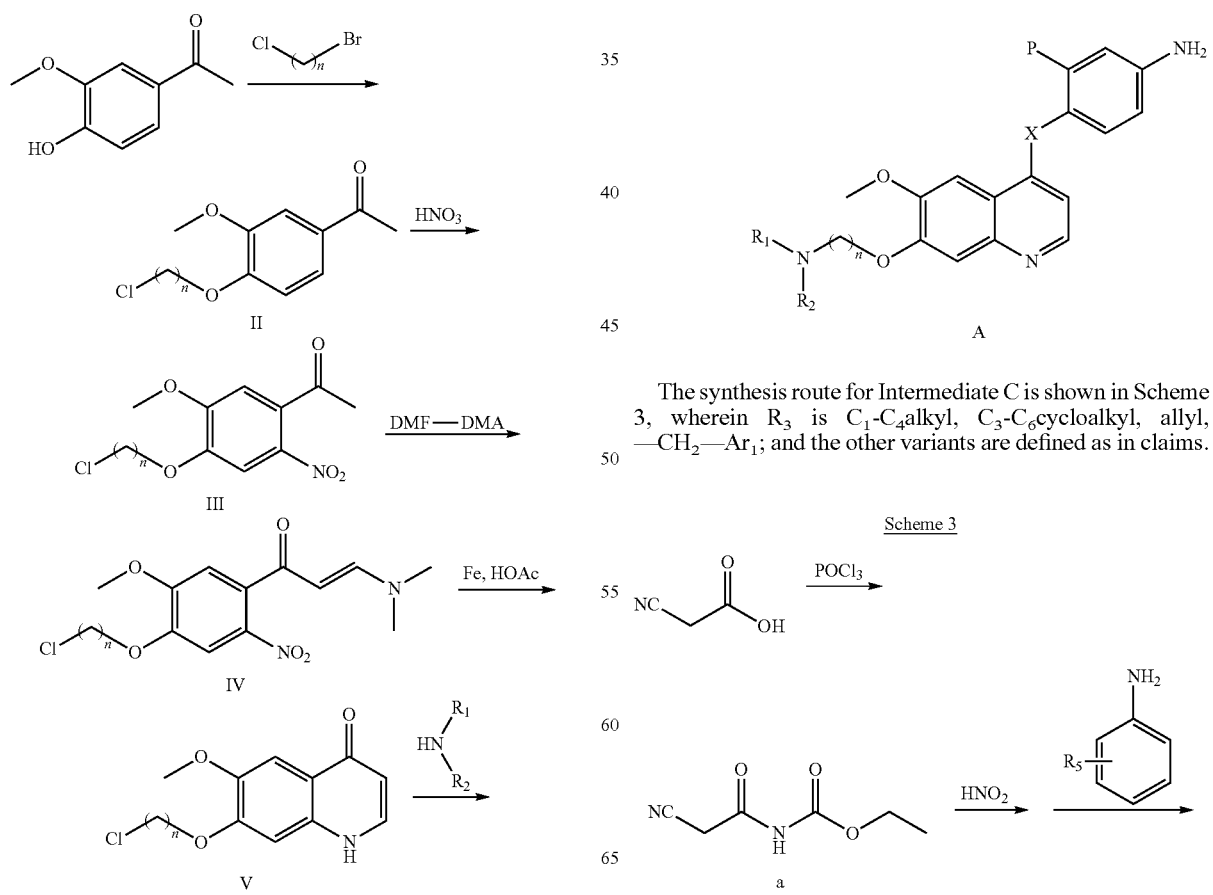
The synthesis route for Intermediate C is shown in Scheme 3, wherein $R_3$ is $C_1$-$C_4$alkyl, $C_3$-$C_6$cycloalkyl, allyl, —$CH_2$—$Ar_1$; and the other variants are defined as in claims.
Scheme 3

-continued

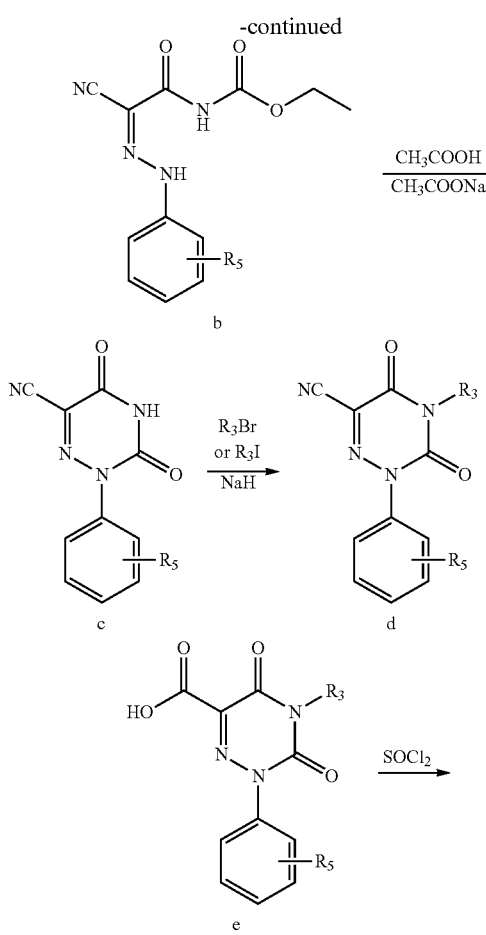

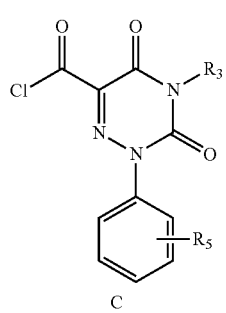

In case that $R_3$ is H, Intermediate C can be obtained by directly hydrolyzing Intermediate c with an acid to produce Intermediate e, and then reacting the obtained Intermediate e and thionyl chloride.

SPECIFIC MODE FOR CARRYING OUT THE INVENTION

The following Examples are given for the purpose of illustrating, rather than limiting, the scope of the present invention. The nuclear magnetic resonance hydrogen spectrum (HNMR) of the compounds of the invention was determined by Bruker ARX-600, and mass spectrum (MS) was determined by Agilent 1100 LC/MSD; all reagents were analytically pure or chemically pure.

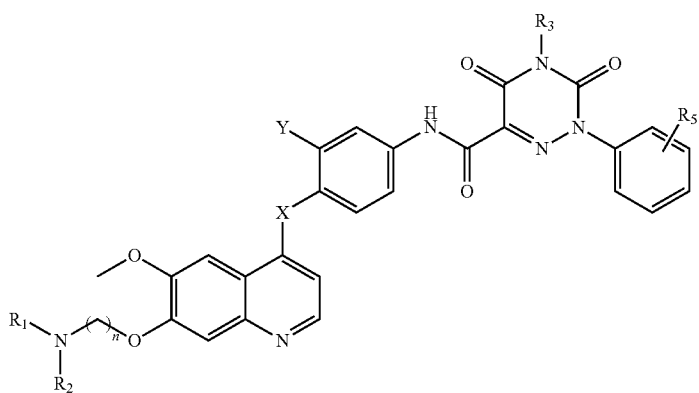

| Example | —NR$_1$R$_2$ | X | Y | n | R$_3$ | Ar |
|---|---|---|---|---|---|---|
| Example 1 | pyrrolidinyl | —O— | —F | 3 | —CH$_3$ | phenyl |
| Example 2 | piperidinyl | —O— | —F | 3 | —CH$_3$ | phenyl |

-continued

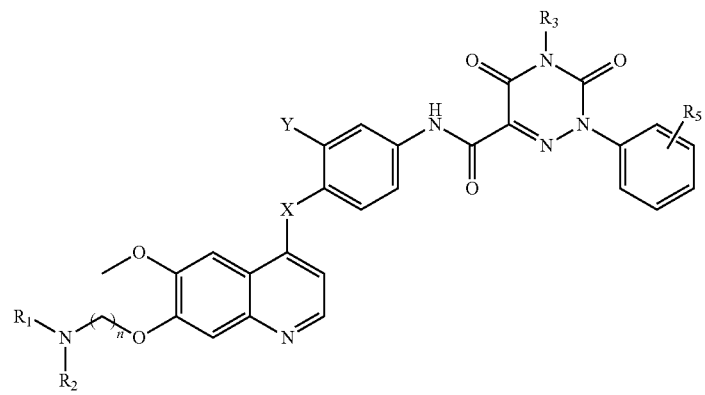

| Example | —NR₁R₂ | X | Y | n | R₃ | Ar |
|---|---|---|---|---|---|---|
| Example 3 | morpholino | —O— | —F | 3 | —CH₃ | phenyl |
| Example 4 | 4-methylpiperidino | —O— | —F | 3 | —CH₃ | phenyl |
| Example 5 | 4-methylpiperazino | —O— | —F | 3 | —CH₃ | phenyl |
| Example 6 | pyrrolidino | —O— | —F | 3 | —CH₃ | 4-F-phenyl |
| Example 7 | piperidino | —O— | —F | 3 | —CH₃ | 4-Br-phenyl |
| Example 8 | morpholino | —O— | —F | 3 | —CH₃ | 4-F-phenyl |
| Example 9 | 4-methylpiperidino | —O— | —F | 3 | —CH₃ | 4-F-phenyl |
| Example 10 | 4-methylpiperazino | —O— | —F | 3 | —CH₃ | 4-F-phenyl |
| Example 11 | pyrrolidino | —O— | —F | 3 | —CH₃ | 4-H₃CO-phenyl |
| Example 12 | piperidino | —O— | —F | 3 | —CH₃ | 4-H₃C-phenyl |

-continued

| Example | —NR₁R₂ | X | Y | n | R₃ | Ar |
|---|---|---|---|---|---|---|
| Example 13 | morpholinyl | —O— | —F | 3 | —CH₃ | 4-methylphenyl |
| Example 14 | 4-methylpiperidinyl | —O— | —F | 3 | —CH₃ | 4-methylphenyl |
| Example 15 | 4-methylpiperazinyl | —O— | —F | 3 | —CH₃ | 4-methylphenyl |
| Example 16 | pyrrolidinyl | —O— | —F | 3 | —CH₃ | 3,4-difluorophenyl |
| Example 17 | piperidinyl | —O— | —F | 3 | —CH₃ | 3,4-difluorophenyl |
| Example 18 | morpholinyl | —O— | —F | 3 | —CH₃ | 3,4-difluorophenyl |
| Example 19 | 4-methylpiperidinyl | —O— | —F | 3 | —CH₃ | 3,4-difluorophenyl |
| Example 20 | 4-methylpiperazinyl | —O— | —F | 3 | —CH₃ | 3,4-difluorophenyl |

-continued

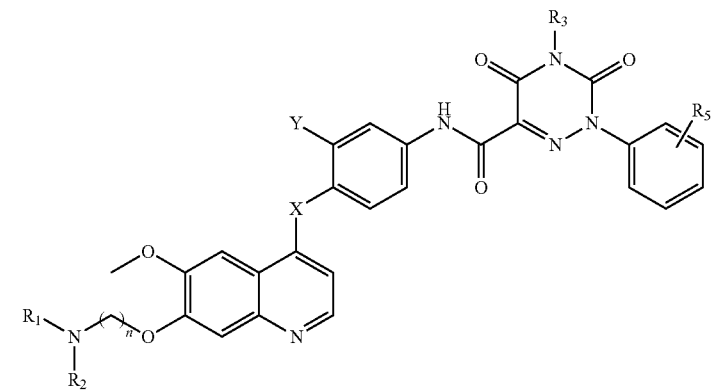

| Example | —NR₁R₂ | X | Y | n | R₃ | Ar |
|---|---|---|---|---|---|---|
| Example 21 | pyrrolidin-1-yl | —O— | —F | 3 | —CH₃ | 3-(F₃C)phenyl |
| Example 22 | piperidin-1-yl | —O— | —F | 3 | —CH₃ | 3-(F₃C)phenyl |
| Example 23 | morpholin-4-yl | —O— | —F | 3 | —CH₃ | 2-F-phenyl |
| Example 24 | 4-methylpiperidin-1-yl | —O— | —F | 3 | —CH₃ | 3-(F₃C)phenyl |
| Example 25 | 4-methylpiperazin-1-yl | —O— | —F | 3 | —CH₃ | 3-(F₃C)phenyl |
| Example 26 | piperidin-1-yl | —O— | —F | 3 | —CH₃ | 4-Cl-phenyl |
| Example 27 | morpholin-4-yl | —O— | —F | 3 | —CH₃ | 4-Cl-phenyl |
| Example 28 | 4-methylpiperidin-1-yl | —O— | —F | 3 | —CH₂CH₂CH₃ | phenyl |

-continued

| Example | —NR$_1$R$_2$ | X | Y | n | R$_3$ | Ar |
|---|---|---|---|---|---|---|
| Example 29 | morpholine (N-linked, O in ring) | —O— | —F | 3 | —CH$_2$CH$_2$CH$_3$ | 2-F-phenyl |
| Example 30 | pyrrolidine (N-linked) | —O— | —F | 3 | —CH$_2$CH$_2$CH$_3$ | 3-F-phenyl |
| Example 31 | 4-methylpiperazine (N-linked) | —O— | —F | 3 | —CH$_2$CH$_2$CH$_3$ | 4-Cl-phenyl |
| Example 32 | piperidine (N-linked) | —O— | —F | 3 | —CH$_2$CH$_2$CH$_3$ | 4-Br-phenyl |
| Example 33 | 4-methylpiperidine (N-linked) | —O— | —F | 3 | —CH$_2$CH$_2$CH$_3$ | 2-CF$_3$-phenyl |
| Example 34 | morpholine (N-linked) | —O— | —F | 3 | —CH$_2$CH$_2$CH$_3$ | 3-CF$_3$-phenyl |
| Example 35 | pyrrolidine (N-linked) | —O— | —F | 3 | —CH$_2$CH$_2$CH$_3$ | 2-CF$_3$-phenyl |
| Example 36 | 4-methylpiperazine (N-linked) | —O— | —F | 3 | —CH$_2$CH=CH$_2$ | 2-CF$_3$-phenyl |

-continued

| Example | —NR₁R₂ | X | Y | n | R₃ | Ar |
|---|---|---|---|---|---|---|
| Example 37 | piperidinyl | —O— | —F | 3 | —CH₂CH=CH₂ | 2-(CF₃)phenyl |
| Example 38 | pyrrolidinyl | —O— | —F | 3 | —CH₂CH=CH₂ | 4-Cl-phenyl |
| Example 39 | morpholinyl | —O— | —F | 3 | —CH₂CH=CH₂ | 4-Br-phenyl |
| Example 40 | piperidinyl | —O— | —F | 3 | —CH₂CH=CH₂ | 2-F-phenyl |
| Example 41 | 4-methylpiperazinyl | —O— | —F | 3 | —CH₂CH=CH₂ | 2-F-phenyl |
| Example 42 | pyrrolidinyl | —O— | —F | 3 | —CH₂CH=CH₂ | 4-F-phenyl |
| Example 43 | morpholinyl | —O— | —F | 3 | —CH₂C₆H₅ | 2,4-diCl-phenyl |
| Example 44 | piperidinyl | —O— | —F | 3 | —CH₂C₆H₅ | 2,4-diF-phenyl |

-continued

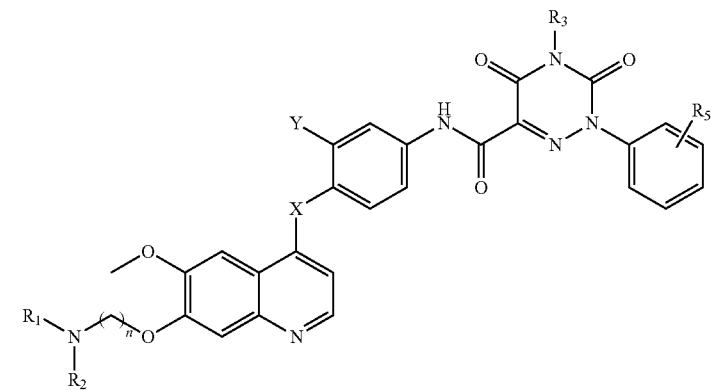

| Example | —NR₁R₂ | X | Y | n | R₃ | Ar |
|---|---|---|---|---|---|---|
| Example 45 | 4-methylpiperazin-1-yl | —O— | —F | 3 | —CH₂C₆H₅ | 3,4-difluorophenyl |
| Example 46 | piperidin-1-yl | —O— | —F | 3 | —CH₂C₆H₅ | phenyl |
| Example 47 | 4-methylpiperazin-1-yl | —O— | —F | 3 | —CH₂C₆H₅ | 3-(trifluoromethyl)phenyl |
| Example 48 | pyrrolidin-1-yl | —O— | —F | 3 | —H | 2,4-dichlorophenyl |
| Example 49 | morpholin-4-yl | —O— | —F | 3 | —H | 2,4-dimethylphenyl |
| Example 50 | piperidin-1-yl | —O— | —F | 3 | —H | 4-fluorophenyl |
| Example 51 | 4-methylpiperazin-1-yl | —O— | —F | 3 | —H | 4-bromophenyl |
| Example 52 | 4-methylpiperidin-1-yl | —O— | —F | 3 | —H | 2-chlorophenyl |

-continued
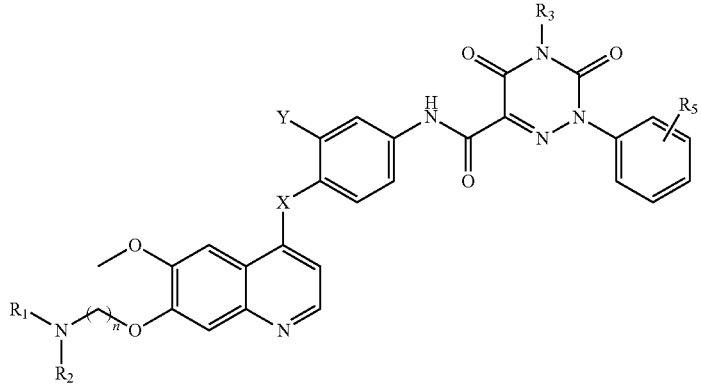
| Example | —NR₁R₂ | X | Y | n | R₃ | Ar |
|---|---|---|---|---|---|---|
| Example 53 | 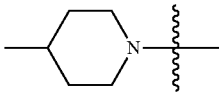 | —O— | —F | 2 | —CH₃ | 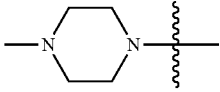 |
| Example 54 | 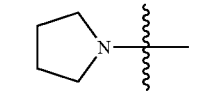 [SMILES: *N1CCCC1] | —O— | —F | 2 | —CH₃ | 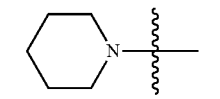 |
| Example 55 | 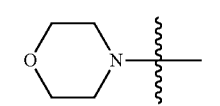 [SMILES: *N1CCOCC1] | —O— | —F | 2 | —CH₃ | 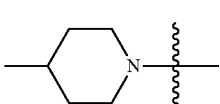 |
| Example 56 | 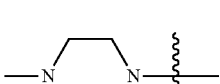 | —O— | —F | 2 | —CH₃ | 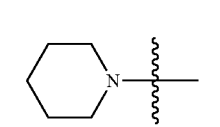 |
| Example 57 | | —O— | —F | 4 | —CH₃ | |
| Example 58 | | —O— | —F | 4 | —CH₃ | |
| Example 59 | | —O— | —F | 4 | —CH₃ | |
| Example 60 | | —O— | —F | 4 | —CH₃ | |

Example 1

N-[3-fluoro-4-[6-methoxy-7-[3-(tetrahydropyrrol-1-yl)propyloxy]phenyl]quinolin-4-oxy]phenyl]-2-phenyl-4-methyl-3,5-dioxo-2,3,4,5-tetrahydro-1,2,4-triazine-6-carboxamide

Step A 1-[4-(3-chloropropyloxy)-3-methoxy]phenylethanone (II)

3-methoxy-4-hydroxyphenylethanone (600 g, 3.61 mol) and anhydrous potassium carbonate (698 g, 5.055 mol) were added to DMF (5v/w, 2500 mL). The mixture was stirred thoroughly at 25° C. for 30 min. Then 1,3-bromochloropane (795.9 g, 1.4 mol) was slowly added dropwise to the mixture. After the dropwise addition, the mixture was reacted under stirring at 25° C. for 10 h. After completion of the reaction, the mixture was filtered by suction. The filtered cake was washed with a small amount of DMF. The filtrate was collected, and slowly poured into ice-water. The mixture was violently stirred to separate out a white solid. The white solid was filtered by suction. The filtered cake was dried to produce a white solid (827.2 g) in a yield of 93.8%.

Step B 1-[4-(3-chloropropyloxy)-5-methoxy-2-nitro]phenylethanone (III)

Intermediate II (200 g, 0.82 Mol) was added to $CH_2Cl_2$ (5v/w, 1000 mL). The mixture was stirred thoroughly so as to dissolve Intermediate II completely. Then, after cooling the reaction solution to −20° C., fuming nitric acid (130 g, 2.06 mol) was slowly added dropwise thereto while keeping the temperature of the reaction solution below −10° C. After the dropwise addition, the reaction was conducted at −20° C. for 2 h. After completion of the reaction, the reaction solution was poured into ice-water. The organic layer was collected, and washed with a saturated saline solution until the aqueous layer became neutral. The organic layer was collected and dried over anhydrous sodium sulfate. Then the solvent was evaporated off to produce a reddish brown oil, which was thoroughly cooled to produce a yellow solid (210 g) in a yield of 89%.

Step C (E)-1-[4-(3-chloropropyloxy)-5-methoxy-2-nitrophenyl]-3-(dimethylamino)prop-2-en-1-one (IV)

Intermediate III (200 g, 0.695 mol) was added to toluene (5v/w, 1000 mL). The mixture was heated to 110° C. so as to dissolve Intermediate III completely. After adding DMF-DMA (414.2 g, 3.476 mol), The mixture was reacted under reflux for 16 h. After completion of the reaction, the reaction solution was cooled to room temperature, and then placed and stirred into a cold trap. A yellow solid separated out and was filtered by suction. The filtered cake was dried to produce a yellow solid (180 g) in a yield of 75.8%.

Step D 7-(3-chloropropyloxy)-6-methoxy-4(1H)-quinolinone (V)

Intermediate IV (150 g, 0.44 mol) was added to glacial acetic acid (8v/w, 1200 mL). The mixture was warmed up to 40° C. After Intermediate IV was dissolved completely, iron powder (123.1 g, 2.20 mol) was slowly added in batch. The mixture was warmed up to 80° C. and reacted under mechanical stirring for 2 h. After completion of the reaction, the reaction solution was filtered by suction when it is still hot. The filtrate was collected. After cooling the filtrate, a great deal of solid separated out and was filtered by suction to produce a lutescens solid. The filtered cake was dissolved in glacial acetic acid. The mixture was stirred at 80° C. for about 30 min, and was filtered by suction again when it is still hot. The filtrate was collected. After cooling the filtrate, a solid separated out and was filtered by suction to produce a lutescens solid. The solids were combined, and washed with water several times until the filtrate became neutral. The filtered cake was dried to produce a pale yellow solid (79 g) in a yield of 65%.

Step E 6-methoxy-7-[3-(1-pyrrolidyl)propyloxy]-4(1H)-quinolinone (VI)

Intermediate V (62 g, 0.232 mol) and tetrahydropyrrole (82.46 g, 1.16 mol) were added to acetonitrile (620 mL). The mixture was heated under reflux for 8 h. After completion of the reaction, a portion of solvent was evaporated off. The reaction vessel was placed in a cold trap. The reaction was filtered by suction. The filtered cake was washed with ethyl acetate to produce a yellow solid (66.74 g) in a yield of 95.3%.

Step F 4-chloro-6-methoxy-7-[3-(1-pyrrolidyl)propyloxy]quinoline (VII)

Intermediate VI (63 g, 0.198 mol) and $POCl_3$ (5v/w, 315 mL) were added to acetonitrile (5v/w, 315 mL). The mixture was warmed up to 85° C. to react under reflux for 6 h. After completion of the reaction, the reaction solution was cooled. $POCl_3$ and acetonitrile were evaporated off to produce a grey viscous solid. This solid was added to a great deal of ice-water mixture, adjusted with a 10% KOH solution to a pH of 10, and extracted with $CH_2Cl_2$ (200 mL×3). The organic layer was collected, dried over anhydrous sodium sulfate, and cooled after evaporating off the solvate to produce an off-white solid (58 g) in a yield of 87.3%.

Step G 4-(2-fluoro-4-nitrophenyloxy)-6-methoxy-7-[3-(1-pyrrolidyl)propyloxy]quinoline (VIII)

2-fluoro-4-nitrophenol (36.73 g, 0.234 mol) was added to a dried chlorobenzene (5v/w, 250 mL). The mixture was heated to 145° C. Intermediate VII (12.5 g, 0.039 mol) was added to the reaction solution. The reaction was conducted at this temperature for 20 h. After completion of the reaction, the solvent was evaporated off to produce a grey solid. This solid was dissolved in $CH_2Cl_2$, and washed with a satureated saturated $K_2CO_3$ solution several times. The organic layer was collected. The solvent was dried off to produce a solid, which is recrystallized with ethanol to produce a yellow solid (49.16 g) in a yield of 71.4%.

Step H 3-fluoro-4-[6-methoxy-7-[3-(1-pyrrolidyl)propyloxy]quinolin-4-oxy]aniline (A-1)

Iron powder (61.42 g, 1.1 mol) and hydrochloric acid (6 mL) were added to 90% EtOH (25v/w, 1210 mL). The mixture was warmed up to 80° C. and stirred for 15 min. Then Intermediate VIII (48.42 g, 0.11 mol) was added in batch to the reaction solution. After the addition completion, the reaction was conducted under reflux for 2 h. After completion of the reaction, the reaction was filtered by suction when it is still hot. The filtrate was collected. The solvate was evaporated off to produce a yellow solid (43 g) in a yield of 95%.

Step I ethyl (2-cyanoacetamido)formate (a)

2-cyanoacetic acid (85 g, 1 mol) and ethyl aminoformate (89 g, 1 mol) were added to toluene (500 mL). To the mixture was slowly added phosphorus oxychloride (45 mL, 0.5 mol), and then added DMF (5 mL). The reaction was conducted at 70° C. for 2 h. After cooling, water (500 mL) was added to the reaction solution to quench phosphorus oxychloride. The reaction is filtered by suction. The filtered cake was washed with ethyl ether and dried to produce a white solid (104 g) in a yield of 67%.

Step J ethyl[2-cyano-2-(2-phenylhydrazono)acetamido]formate (b)

Aniline (10.3 g, 0.11 mol) and hydrochloric acid (45 mL, 0.56 mol) were added to water (400 mL). The mixture was stirred and cooled down to 0° C. To the mixture was added dropwise an aqueous solution of $NaNO_2$ (7.73 g, 0.11 mol) while controlling the temperature between 0 and 5° C. After the dropwise addition, the reaction was conducted at a temperature between 0 and 5° C. for 30 min. The obtained solution was reserved for future use.

Intermediate a and sodium acetate (80 g, 0.98 mol) were added to ethanol (400 mL). The mixture was stirred and cooled down to 0° C. To the solution of Intermediate a was added dropwise the reserved solution while controlling the temperature between 0 and 5° C. After the dropwise addition, the reaction was conducted at a temperature between 0 and 5° C. for 2 h. The reaction is filtered by suction. The filtered cake was washed with water and dried to produce an orange solid (21.5 g) in a yield of 91.1%.

Step K 2-phenyl-3,5-dioxo-2,3,4,5-tetrahydro-1,2,4-triazine-6-carbonitrile (c)

Intermediate b (21 g, 0.08 mol) and anhydrous sodium acetate (29 g, 0.35 mol) were added to glacial acetic acid (20v/w, 420 mL). The mixture was warmed up to react under reflux for 2 h. After completion of the reaction, the reaction solution was cooled to 0° C. and poured into water (1200 mL). The mixture was stirred for 30 min and filtered by suction. The filtered cake was washed with water and petroleum ether, and dried to produce an orange red solid (12 g) in a yield of 67.8%.

Step L 2-phenyl-4-methyl-3,5-dioxo-2,3,4,5-tetrahydro-1,2,4-triazine-6-carbonitrile (d)

Intermediate c (9 g, 0.042 mol) was added to DMF (100 mL). To the mixture was added NaH (1.3 g, 0.054 mol) in batch under an ice bath. After stirring for 30 min, methyl iodide (2.74 mL, 0.042 mol) was added dropwise. After the dropwise addition, the reaction was conducted for 2 h. After completion of the reaction, the reaction solution was poured into water (600 mL). A great deal of red solid separated out and was filtered by suction. The filtered cake was washed with water and dried to produce an orange red solid (7.6 g) in a yield of 80.0%.

Step M 2-phenyl-4-methyl-3,5-dioxo-2,3,4,5-tetrahydro-1,2,4-triazine-6-carboxylic acid (e)

Intermediate d (7.6 g, 0.033 mol) was added to a mixed solvent of glacial acetic acid (100 mL) and HCl (72 mL, 0.86 mol). The mixture was warmed up to 120° C. and reacted under reflux for 4 h. The solvent was evaporated off. To the obtained fraction was added water (400 mL). The mixture was filtered by suction and dried to produce a solid (3.7 g) in a yield of 45.7%.

Step N 2-phenyl-4-methyl-3,5-dioxo-2,3,4,5-tetrahydro-1,2,4-triazine-6-carbonyl chloride (C-1)

Intermediate e (3 g, 0.012 mol) was added to thionyl chloride (10V/W, 30 mL). The mixture was warmed up to react under reflux for 6 h. The solvent was evaporated off to produce a clear yellow crystal (2.8 g) in a yield of 87.5%.

Step O N-[3-fluoro-4-[6-methoxy-7-[3-(tetrahydropyrrol-1-yl)propyloxy]quinolin-4-oxy]phenyl]-2-phenyl-4-methyl-3,5-dioxo-2,3,4,5-tetrahydro-1,2,4-triazine-6-carboxamide (Example 1)

Compound A-1 (0.2 g, 0.48 mmol), Compound C-1 (0.15 g, 0.58 mmol), and N,N-diisopropylethylamine (0.07 g, 0.58 mmol) were added to dried dichloromethane (10 mL). The reaction was conducted at room temperature for 10 h. After completion of the reaction, the organic layer was washed with 5% aqueous potassium carbonate solution and a saturated saline solution, dried over anhydrous magnesium sulfate, and evaporated off to produce a compound named N-[3-fluoro-4-[6-methoxy-7-[3-(tetrahydropyrrol-1-yl)propyloxy]quinolin-4-oxy]phenyl]-2-phenyl-4-methyl-3,5-dioxo-2,3,4,5-tetrahydro-1,2,4-triazine-6-carboxamide (Example 1) (0.24 g) in a yield of 80.2%.

ESI-MS [M+H] (m/z): 669.7; $^1$H NMR (300 MHz, DMSO) δ 11.34 (s, 1H), 8.05 (dd, J=12.7, 2.0 Hz, 1H), 7.80 (d, J=6.6 Hz, 2H), 7.76-7.42 (m, 8H), 7.02 (d, J=6.3 Hz, 1H), 4.38 (t, 2H), 4.07 (s, 3H), 3.66-3.44 (m, 9H), 3.44-3.33 (m, 4H), 2.85 (s, 3H), 2.44-2.34 (m, 2H).

According to the procedure of Example 1, the anilines with different substitutents as starting material and Intermediate a were subjected to five reaction steps including diazotization to finally produce Compounds C-1 with different substitutents, which were further reacted with Compounds A-1 with different substituents to produce compounds of Examples 2-27.

Example 2

N-[3-fluoro-4-[6-methoxy-7-[3-(1-piperidinyl)propyloxy]quinolin-4-oxy]phenyl]-2-phenyl-4-methyl-3,5-dioxo-2,3,4,5-tetrahydro-1,2,4-triazine-6-carboxamide ESI-MS [M+H] (m/z): 656.7; $^1$H NMR (300 MHz, DMSO) δ 11.34 (s, 1H), 8.05 (dd, J=12.7, 2.0 Hz, 1H), 7.80 (d, J=6.6 Hz, 2H), 7.76-7.42 (m, 8H), 7.02 (d, J=6.3 Hz, 1H), 4.38 (t, 2H), 4.07 (s, 3H), 3.66-3.44 (m, 6H), 3.44-3.33 (m, 4H), 2.85 (s, 3H), 2.44-2.34 (m, 2H).

Example 3

N-[3-fluoro-4-[6-methoxy-7-[3-(4-morpholinyl)propyloxy]quinolin-4-oxy]phenyl]-2-phenyl-4-methyl-3,5-dioxo-2,3,4,5-tetrahydro-1,2,4-triazine-6-carboxamide ESI-MS [M+H] (m/z):658.7; $^1$H NMR (300 MHz, DMSO) δ 10.95 (s, 1H), 8.48 (d, J=5.2 Hz, 1H), 7.94 (dd, 1H), 7.67-7.57 (m, 3H), 7.55 (s, 1H), 7.49 (t, J=8.9 Hz, 1H), 7.43-7.36 (m, 3H), 6.49 (d, J=5.2 Hz, 1H), 4.23 (t, J=6.3 Hz, 2H), 3.96 (s, 3H), 2.73 (d, J=26.2 Hz, 6H), 2.5 (S, 3H), 2.10-1.98 (m, 2H), 1.81-1.73 (m, 4H).

Example 4

N-[3-fluoro-4-[6-methoxy-7-[3-(4-methyl-1-piperidinyl)propyloxy]quinolin-4-oxy]phenyl]-2-phenyl-4-methyl-3,5-dioxo-2,3,4,5-tetrahydro-1,2,4-triazine-6-carboxamide ESI-MS [M+H] (m/z): 674.7; $^1$H NMR (300 MHz, DMSO) δ 10.98 (s, 1H), 8.48 (d, J=5.2 Hz, 1H), 7.95 (dd, J=12.8, 2.1 Hz, 1H), 7.68-7.57 (m, 3H), 7.54 (s, 1H), 7.49 (t, J=8.9 Hz, 1H), 7.40 (dd, J=11.6, 5.9 Hz, 3H), 6.49 (d, J=5.1 Hz, 1H), 4.21 (t, J=6.3 Hz, 2H), 3.96 (s, 3H), 3.65-3.56 (m, 4H), 2.51 (dd, J=6.5, 4.7 Hz, 5H), 2.47-2.37 (m, 4H), 2.06-1.92 (m, 2H).

Example 5

N-[3-fluoro-4-[6-methoxy-7-[3-(4-methyl-1-piperazinyl)propyloxy]quinolin-4-oxy]phenyl]-2-phenyl-4-methyl-3,5-dioxo-2,3,4,5-tetrahydro-1,2,4-triazine-6-carboxamide ESI-MS [M+H] (m/z): 686.7; $^1$H NMR (300 MHz, DMSO) δ 10.94 (s, 1H), 8.48 (d, J=5.2 Hz, 1H), 7.67-7.56 (m, 2H), 7.50 (dd, J=15.8, 7.0 Hz, 2H), 7.50 (dd, J=15.8, 7.0 Hz, 2H), 7.43-7.35 (m, 3H), 6.49 (d, J=5.2 Hz, 1H), 4.19 (t, J=6.4 Hz, 2H), 3.95 (s, 3H), 3.31 (s, 3H), 2.85 (d, J=11.1 Hz, 2H), 2.45 (t, J=7.0 Hz, 2H), 2.02-1.82 (m, 4H), 1.58 (d, J=11.9 Hz, 2H), 1.38-1.24 (m, 1H), 1.22-1.07 (m, 2H), 0.89 (d, J=6.4 Hz, 3H).

Example 6

N-[3-fluoro-4-[6-methoxy-7-[3-(1-pyrrolidyl)propyloxy]quinolin-4-oxy]phenyl]-2-(4-fluorophenyl)-4-methyl-3,5-dioxo-2,3,4,5-tetrahydro-1,2,4-triazine-6-carboxamide ESI-MS [M+H] (m/z):658.7.

Example 7

N-[3-fluoro-4-[6-methoxy-7-[3-(1-piperidinyl)propyloxy]quinolin-4-oxy]phenyl]-2-(4-bromophenyl)-4-methyl-3,5-dioxo-2,3,4,5-tetrahydro-1,2,4-triazine-6-carboxamide ESI-MS [M+H] (m/z):733.5.

Example 8

N-[3-fluoro-4-[6-methoxy-7-[3-(4-morpholinyl)propyloxy]quinolin-4-oxy]phenyl]-2-(4-fluorophenyl)-4-methyl-3,5-dioxo-2,3,4,5-tetrahydro-1,2,4-triazine-6-carboxamide ESI-MS [M+H] (m/z): 674.7.

Example 9

N-[3-fluoro-4-[6-methoxy-7-[3-(4-methyl-1-piperidinyl)propyloxy]quinolin-4-oxy]phenyl]-2-(4-fluorophenyl)-4-methyl-3,5-dioxo-2,3,4,5-tetrahydro-1,2,4-triazine-6-carboxamide ESI-MS [M+H] (m/z): 686.7.

Example 10

N-[3-fluoro-4-[6-methoxy-7-[3-(4-methyl-1-piperazinyl)propyloxy]quinolin-4-oxy]phenyl]-2-(4-fluorophenyl)-4-methyl-3,5-dioxo-2,3,4,5-tetrahydro-1,2,4-triazine-6-carboxamide ESI-MS [M+H] (m/z): 687.7.

Example 11

N-[3-fluoro-4-[6-methoxy-7-[3-(1-pyrrolidyl)propyloxy]quinolin-4-oxy]phenyl]-2-(4-methoxyphenyl)-4-methyl-3,5-dicarbonyl-2,3,4,5-tetrahydro-1,2,4-triazine-6-carboxamide ESI-MS [M+H] (m/z): 670.7.

Example 12

N-[3-fluoro-4-[6-methoxy-7-[3-(1-piperidinyl)propyloxy]quinolin-4-oxy]phenyl]-2-(4-methylphenyl)-4-methyl-3,5-dicarbonyl-2,3,4,5-tetrahydro-1,2,4-triazine-6-carboxamide ESI-MS [M+H] (m/z): 668.7.

Example 13

N-[3-fluoro-4-[6-methoxy-7-[3-(4-morpholinyl)propyloxy]quinolin-4-oxy]phenyl]-2-(4-methylphenyl)-4-methyl-3,5-dicarbonyl-2,3,4,5-tetrahydro-1,2,4-triazine-6-carboxamide ESI-MS [M+H] (m/z): 670.7.

Example 14

N-[3-fluoro-4-[6-methoxy-7-[3-(4-methyl-1-piperidinyl)propyloxy]quinolin-4-oxy]phenyl]-2-(4-methylphenyl)-4-methyl-3,5-dicarbonyl-2,3,4,5-tetrahydro-1,2,4-triazine-6-carboxamide ESI-MS [M+H] (m/z): 682.7.

Example 15

N-[3-fluoro-4-[6-methoxy-7-[3-(4-methyl-1-piperazinyl)propyloxy]quinolin-4-oxy]phenyl]-2-(4-methylphenyl)-4-methyl-3,5-dicarbonyl-2,3,4,5-tetrahydro-1,2,4-triazine-6-carboxamide ESI-MS [M+H] (m/z):683.7.

Example 16

N-[3-fluoro-4-[6-methoxy-7-[3-(1-pyrrolidyl)propyloxy]quinolin-4-oxy]phenyl]-2-(3,4-difluorophenyl)-4-methyl-3,5-dioxo-2,3,4,5-tetrahydro-1,2,4-triazine-6-carboxamide ESI-MS [M+H] (m/z): 676.7.

Example 17

N-[3-fluoro-4-[6-methoxy-7-[3-(1-piperidinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide ESI-MS [M+H] (m/z): 690.7.

Example 18

N-[3-fluoro-4-[6-methoxy-7-[3-(4-morpholinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide ESI-MS [M+H] (m/z): 692.7.

Example 19

N-[3-fluoro-4-[6-methoxy-7-[3-(4-methylpiperidin-1-yl)propyloxy]quinolin-4-oxy]phenyl]-2-(3,4-difluorophenyl)-4-methyl-3,5-dioxo-2,3,4,5-tetrahydro-1,2,4-triazine-6-carboxamide ESI-MS [M+H] (m/z): 704.7.

Example 20

N-[3-fluoro-4-[6-methoxy-7-[3-(4-methyl-1-piperazinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide ESI-MS [M+H] (m/z): 705.7.

Example 21

N-[3-fluoro-4-[6-methoxy-7-[3-(1-pyrrolidyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide ESI-MS [M+H] (m/z): 708.7.

Example 22

N-[3-fluoro-4-[6-methoxy-7-[3-(1-piperidinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide ESI-MS [M+H] (m/z): 722.7.

Example 23

N-[3-fluoro-4-[6-methoxy-7-[3-(4-morpholinyl)propyloxy]quinolin-4-oxy]phenyl]-2-(2-fluorophenyl)-4-methyl-3,5-dicarbonyl-2,3,4,5-tetrahydro-1,2,4-triazine-6-carboxamide ESI-MS [M+H] (m/z): 674.6.

Example 24

N-[3-fluoro-4-[6-methoxy-7-[3-(4-methyl-1-piperidinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide ESI-MS [M+H] (m/z): 736.7.

Example 25

N-[3-fluoro-4-[6-methoxy-7-[(3-(4-methyl-1-piperazinyl)propyloxy)quinolin-4-oxy]phenyl]-2-(3-trifluoromethylphenyl)-4-methyl-3,5-dicarbonyl-2,3,4,5-tetrahydro-1,2,4-triazine-6-carboxamide ESI-MS [M+H] (m/z): 737.7.

Example 26

N-[3-fluoro-4-[6-methoxy-7-[3-(1-piperidinyl)propyloxy]quinolin-4-oxy]phenyl]-2-(4-chlorophenyl)-4-methyl-3,5-dioxo-2,3,4,5-tetrahydro-1,2,4-triazine-6-carboxamide ESI-MS [M+H] (m/z): 689.1.

Example 27

N-[3-fluoro-4-[6-methoxy-7-[3-(4-morpholinyl)propyloxy]quinolin-4-oxy]phenyl]-2-(4-chlorophenyl)-4-methyl-3,5-dioxo-2,3,4,5-tetrahydro-1,2,4-triazine-6-carboxamide ESI-MS [M+H] (m/z): 691.1.

Example 28

N-[3-fluoro-4-[7-methoxy-6-[3-(4-methyl-1-piperidinyl)propyloxy]quinolin-4-oxy]phenyl]-2-phenyl-4-butyl-3,5-dioxo-2,3,4,5-tetrahydro-1,2,4-triazine-6-carboxamide Step P 2-phenyl-4-butyl-3,5-dioxo-2,3,4,5-tetrahydro-1,2,4-triazine-6-carbonitrile (f)

Intermediate c (9 g, 0.042 mol) was added to DMF (100 mL). To the mixture was added NaH (1.3 g, 0.054 mol) in batch under an ice bath. After stirring for 30 min, n-butyl bromide (3.4 mL, 0.042 mol) was added dropwise. After the dropwise addition, the reaction was conducted at 70° C. for 6 h. After completion of the reaction, the reaction solution was poured into water (600 mL). A great deal of solid separated out and was filtered by suction. The filtered cake was washed with water and dried to produce Intermediate f (8.2 g) in a yield of 81.4%.

Step Q 2-phenyl-4-butyl-3,5-dioxo-2,3,4,5-tetrahydro-1,2,4-triazine-6-carboxylic acid (g)

Intermediate f (8.2 g, 0.035 mol) was added to a mixed solvent of glacial acetic acid (100 mL) and HCl (72 mL, 0.86 mol). The mixture was warmed up to 120° C. and reacted under reflux for 4 h. The solvent was evaporated off. To the obtained fraction was added water (200 mL). The mixture was filtered by suction and dried to produce Intermediate g (3.7 g) in a yield of 45.7%.

Step R 2-phenyl-4-methyl-3,5-dioxo-2,3,4,5-tetrahydro-1,2,4-triazine-6-carbonyl chloride (Q-2)

Intermediate g (3.0 g, 0.01 mol) was added to thionyl chloride (10V/W, 30 mL). The mixture was warmed up under stirring to react under reflux for 6 h. The solvent was evaporated off to produce a clear yellow crystal (3 g) in a yield of 88%.

Step S N-[3-fluoro-4-[7-methoxy-6-[3-(4-methyl-1-piperidinyl)propyloxy]quinolin-4-oxy]phenyl]-2-phenyl-4-butyl-3,5-dioxo-2,3,4,5-tetrahydro-1,2,4-triazine-6-carboxamide (Example 28)

Compound A-1 (0.2 g, 0.48 mmol), Compound C-2 (0.16 g, 0.58 mmol), and N,N-diisopropylethylamine (0.07 g, 0.58 mmol) were added to dried dichloromethane (10 mL). The reaction was conducted at room temperature for 10 h. After completion of the reaction, the organic layer was washed with 5% aqueous potassium carbonate solution and a saturated saline solution, dried over anhydrous magnesium sulfate, and evaporated off to produce a compound named N-[3-fluoro-4-[7-methoxy-6-[3-(4-methyl-1-piperidinyl)propyloxy]quinolin-4-oxy]phenyl]-2-phenyl-4-butyl-3,5-dioxo-2,3,4,5-tetrahydro-1,2,4-triazine-6-carboxamide (Example 28) (0.24 g) in a yield of 80.2%.

ESI-MS [M+H] (m/z): 710.7.

According to the procedure of Example 28, Intermediate c with different substitutents as starting material was subjected to three reaction steps including butylation, hydrolysis and acylation to finally produce Compound C-2 with different substitutents, which was further reacted with Compound A-1 with different substitutents to produce compounds of Examples 29-35.

Example 29

N-[3-fluoro-4-[7-methoxy-6-[3-(4-morpholinyl)propyloxy]quinolin-4-oxy]phenyl]-2-(2-fluorophenyl)-4-butyl-3,5-dioxo-2,3,4,5-tetrahydro-1,2,4-triazine-6-carboxamide ESI-MS [M+H] (m/z): 716.7.

Example 30

N-[3-fluoro-4-[7-methoxy-6-[3-(1-pyrrolidyl)propyloxy]quinolin-4-oxy]phenyl]-2-(3-fluorophenyl)-4-butyl-3,5-dioxo-2,3,4,5-tetrahydro-1,2,4-triazine-6-carboxamide ESI-MS [M+H] (m/z): 700.7.

Example 31

N-[3-fluoro-4-[7-methoxy-6-[3-(4-methyl-1-piperazinyl)propyloxy]quinolin-4-oxy]phenyl]-2-(4-chlorophenyl)-4-butyl-3,5-dioxo-2,3,4,5-tetrahydro-1,2,4-triazine-6-carboxamide ESI-MS [M+H] (m/z): 746.2.

Example 32

N-[3-fluoro-4-[7-methoxy-6-[3-(1-piperidinyl)propyloxy]quinolin-4-oxy]phenyl]-2-(4-bromophenyl)-4-butyl-3,5-dioxo-2,3,4,5-tetrahydro-1,2,4-triazine-6-carboxamide ESI-MS [M+H] (m/z): 775.6.

Example 33

N-[3-fluoro-4-[7-methoxy-6-[3-(4-methyl-1-piperidinyl)propyloxy]quinolin-4-oxy]phenyl]-2-(2-trifluoromethylphenyl)-4-butyl-3,5-dicarbonyl-2,3,4,5-tetrahydro-1,2,4-triazine-6-carboxamide ESI-MS [M+H] (m/z): 778.7.

Example 34

N-[3-fluoro-4-[7-methoxy-6-[3-(4-morpholinyl)propyloxy]quinolin-4-oxy]phenyl]-2-(3-trifluoromethylphenyl)-4-butyl-3,5-dicarbonyl-2,3,4,5-tetrahydro-1,2,4-triazine-6-carboxamide ESI-MS [M+H] (m/z): 778.7.

Example 35

N-[3-fluoro-4-[7-methoxy-6-[3-(1-pyrrolidyl)propyloxy]quinolin-4-oxy]phenyl]-2-(2-trifluoromethylphenyl)-4-butyl-3,5-dicarbonyl-2,3,4,5-tetrahydro-1,2,4-triazine-6-carboxamide ESI-MS [M+H] (m/z): 750.7.

Example 36

N-[3-fluoro-4-[7-methoxy-6-[3-(4-methyl-1-piperidinyl)propyloxy]quinolin-4-oxy]phenyl]-2-(2-trifluoromethylphenyl)-4-allyl-3,5-dioxo-2,3,4,5-tetrahydro-1,2,4-triazine-6-carboxamide Step T 2-phenyl-4-propenyl-3,5-dioxo-2,3,4,5-tetrahydro-1,2,4-triazine-6-carbonitrile (h)

Intermediate c (9 g, 0.042 mol) was added to DMF (80 mL) under an ice bath. To the mixture was added NaH (1.3 g, 0.054 mol) in batch under an ice bath. After stirring for 30 min, 3-bromopropylene (2.9 mL, 0.042 mol) was added dropwise. After the dropwise addition, the reaction was conducted at 50° C. for 4 h. After completion of the reaction, the reaction solution was poured into water (300 mL). A great deal of solid separated out and was filtered by suction. The filtered cake was washed with water and dried to produce Intermediate f (7.9 g) in a yield of 82%.

Step U 2-phenyl-4-propenyl-3,5-dioxo-2,3,4,5-tetrahydro-1,2,4-triazine-6-carboxylic acid (i)

Intermediate h (8 g, 0.035 mol) was added to a mixed solvent of glacial acetic acid (100 mL) and HCl (72 mL, 0.86 mol). The mixture was warmed up to 120° C. and reacted under reflux for 4 h. The solvent was evaporated off. To the obtained fraction was added water (200 mL). The mixture was filtered by suction and dried to produce Intermediate g (4.2 g) in a yield of 58%.

Step V 2-phenyl-4-propenyl-3,5-dioxo-2,3,4,5-tetrahydro-1,2,4-triazine-6-carbonyl chloride (C-3)

Intermediate I (3.0 g, 0.01 mol) was added to thionyl chloride (10V/W, 30 mL). The mixture was warmed up under stirring to react under reflux for 6 h. The solvent was evaporated off to produce a clear yellow crystal (2.9 g) in a yield of 85%.

Step W N-[3-fluoro-4-[7-methoxy-6-[3-(4-methyl-1-piperidinyl)propyloxy]quinolin-4-oxy]phenyl]-2-(2-trifluoromethylphenyl)-4-allyl-3,5-dioxo-2,3,4,5-tetrahydro-1,2,4-triazine-6-carboxamide (Example 36)

Compound A-1 (0.2 g, 0.50 mmol), Compound C-3 (0.16 g, 0.58 mmol), and N,N-diisopropylethylamine (0.07 g, 0.58 mmol) were added to dried dichloromethane (10 mL). The reaction was conducted at room temperature for 10 h. After completion of the reaction, the organic layer was washed with 5% aqueous potassium carbonate solution and a saturated saline solution, dried over anhydrous magnesium sulfate, and evaporated off to produce a compound named N-[3-fluoro-4-[7-methoxy-6-[3-(4-methyl-1-piperidinyl)propyloxy]quinolin-4-oxy]phenyl]-2-phenyl-4-butyl-3,5-dioxo-2,3,4,5-tetrahydro-1,2,4-triazine-6-carboxamide (Example 36) (0.28 g) in a yield of 86%.

ESI-MS [M+H] (m/z): 762.7.

According to the procedure of Example 36, Intermediate c with different substitutents as starting material was subjected to three reaction steps including propenylation, hydrolysis and acylation to finally produce Compound C-3 with different substitutents, which was further reacted with Compound A-1 with different substituents to produce compounds of Examples 36-42.

Example 37

N-[3-fluoro-4-[7-methoxy-6-[3-(1-piperidinyl)propyloxy]quinolin-4-oxy]phenyl]-2-(2-trifluoromethylphenyl)-4-allyl-3,5-dicarbonyl-2,3,4,5-tetrahydro-1,2,4-triazine-6-carboxamide ESI-MS [M+H] (m/z): 748.7.

Example 38

N-[3-fluoro-4-[6-methoxy-7-[3-(1-pyrrolidyl)propyloxy]quinolin]-4-oxy]phenyl]-2-(4-chlorophenyl)-4-allyl-3,5-dicarbonyl-2,3,4,5-tetrahydro-1,2,4-triazine-6-carboxamide ESI-MS [M+H] (m/z): 701.1.

Example 39

N-[3-fluoro-4-[6-methoxy-7-[3-(4-morpholinyl)propyloxy]quinolin]-4-oxy]phenyl]-2-(4-bromophenyl)-4-allyl-3,5-dicarbonyl-2,3,4,5-tetrahydro-1,2,4-triazine-6-carboxamide ESI-MS [M+H] (m/z): 761.5.

Example 40

N-[3-fluoro-4-[6-methoxy-7-[3-(1-piperidinyl)propyloxy]quinolin]-4-oxy]phenyl]-2-(2-fluorophenyl)-4-allyl-3,5-dicarbonyl-2,3,4,5-tetrahydro-1,2,4-triazine-6-carboxamide ESI-MS [M+H] (m/z): 698.7.

Example 41

N-[3-fluoro-4-[6-methoxy-7-[3-(4-methyl-1-piperazinyl)propyloxy]quinolin]-4-oxy]phenyl]-2-(2-fluorophenyl)-4-allyl-3,5-dicarbonyl-2,3,4,5-tetrahydro-1,2,4-triazine-6-carboxamide ESI-MS [M+H] (m/z): 713.7.

Example 42

N-[3-fluoro-4-[6-methoxy-7-[3-(1-pyrrolidyl)propyloxy]quinolin]-4-oxy]phenyl]-2-(4-fluorophenyl)-4-allyl-3,5-dicarbonyl-2,3,4,5-tetrahydro-1,2,4-triazine-6-carboxamide ESI-MS [M+H] (m/z): 684.6.

Example 43

N-[3-fluoro-4-[6-methoxy-7-[3-(4-morpholinyl)propyloxy]quinolin]-4-oxy]phenyl]-2-(2,4-dichlorophenyl)-4-benzyl-3,5-dicarbonyl-2,3,4,5-tetrahydro-1,2,4-triazine-6-carboxamide Step X 2-phenyl-4-benzyl-3,5-dioxo-2,3,4,5-tetrahydro-1,2,4-triazine-6-carbonitrile (j)

Intermediate c (9 g, 0.042 mol) was added to DMF (80 mL) under an ice bath. To the mixture was added NaH (1.3 g, 0.054 mol) in batch under an ice bath. After stirring for 30 min, benzyl bromide (3.1 mL, 0.042 mol) was added dropwise. After the dropwise addition, the reaction was conducted at 50° C. for 4 h. After completion of the reaction, the reaction solution was poured into water (300 mL). A great deal of solid separated out and was filtered by suction. The filtered cake was washed with water and dried to produce Intermediate j (8.1 g) in a yield of 81%.

Step Y 2-phenyl-4-benzyl-3,5-dioxo-2,3,4,5-tetrahydro-1,2,4-triazine-6-carboxylic acid (k)

Intermediate j (9.2 g, 0.035 mol) was added to a mixed solvent of glacial acetic acid (100 mL) and HCl (72 mL, 0.86 mol). The mixture was warmed up to 120° C. and reacted under reflux for 4 h. The solvent was evaporated off. To the obtained fraction was added water (200 mL). The mixture was filtered by suction and dried to produce Intermediate g (6.5 g) in a yield of 55%.

Step Z 2-phenyl-4-benzyl-3,5-dioxo-2,3,4,5-tetrahydro-1,2,4-triazine-6-carbonyl chloride (C-4)

Intermediate k (3.0 g, 0.01 mol) was added to thionyl chloride (10V/W, 30 mL). The mixture was warmed up under stirring to react under reflux for 6 h. The solvent was evaporated off to produce a clear yellow crystal (2.8 g) in a yield of 81%.

Step Z-1 N-[3-fluoro-4-[7-methoxy-6-[3-(4-morpholinyl)propyloxy]quinolin-4-oxy]phenyl]-2-(2,4-dichlorophenyl)-4-benzyl-3,5-dioxo-2,3,4,5-tetrahydro-1,2,4-triazine-6-carboxamide Example 43

Compound A-1 (0.2 g, 0.50 mmol), Compound C-4 (0.18 g, 0.58 mmol), and N,N-diisopropylethylamine (0.07 g, 0.58 mmol) were added to dried dichloromethane (10 mL). The reaction was conducted at room temperature for 10 h. After completion of the reaction, the organic layer was washed with 5% aqueous potassium carbonate solution and a saturated saline solution, dried over anhydrous magnesium sulfate, and evaporated off to produce a compound named N-[3-fluoro-4-[7-methoxy-6-[3-(4-morpholinyl)propyloxy]quinolin-4-oxy]phenyl]-2-(2,4-dichlorophenyl)-4-benzyl-3,5-dioxo-2,3,4,5-tetrahydro-1,2,4-triazine-6-carboxamide (Example 43) (0.28 g) in a yield of 86%.

ESI-MS [M+H] (m/z): 801.6.

According to the procedure of Example 43, Intermediate c with different substitutents as starting material was subjected to three reaction steps, including propenylation, hydrolysis and acylati, on to finally produce Compound C-4 with different substitutents, which was further reacted with Compound A-1 with different substitutents to produce compounds of Examples 44-47.

Example 44

N-[3-fluoro-4-[6-methoxy-7-[3-(1-piperidinyl)propyloxy]quinolin]-4-oxy]phenyl]-2-(2,4-difluorophenyl)-4-benzyl-3,5-dicarbonyl-2,3,4,5-tetrahydro-1,2,4-triazine-6-carboxamide ESI-MS [M+H] (m/z): 766.7.

Example 45

N-[3-fluoro-4-[6-methoxy-7-[3-(4-methyl-1-piperazinyl)propyloxy]quinolin]-4-oxy]phenyl]-2-(3,4-difluorophenyl)-4-benzyl-3,5-dicarbonyl-2,3,4,5-tetrahydro-1,2,4-triazine-6-carboxamide ESI-MS [M+H] (m/z): 781.7.

Example 46

N-[3-fluoro-4-[6-methoxy-7-[3-(1-piperidinyl)propyloxy]quinolin]-4-oxy]phenyl]-2-phenyl-4-benzyl-3,5-dicarbonyl-2,3,4,5-tetrahydro-1,2,4-triazine-6-carboxamide ESI-MS [M+H] (m/z): 730.7.

Example 47

N-[3-fluoro-4-[6-methoxy-7-[3-(4-methyl-1-piperazinyl)propyloxy]quinolin]-4-oxy]phenyl]-2-(3-trifluoromethylphenyl)-4-benzyl-3,5-dicarbonyl-2,3,4,5-tetrahydro-1,2,4-triazine-6-carboxamide ESI-MS [M+H] (m/z): 813.8.

Example 48

N-[3-fluoro-4-[6-methoxy-7-[3-(1-pyrrolidyl)propyloxy]quinolin]-4-oxy]phenyl]-2-(2,4-dichlorophenyl)-3,5-dicarbonyl-2,3,4,5-tetrahydro-1,2,4-triazine-6-carboxamide Step Z-a 2-phenyl-3,5-dioxo-2,3,4,5-tetrahydro-1,2,4-triazine-6-carboxylic acid (I)

Intermediate c (7.5 g, 0.035 mol) was added to a mixed solvent of glacial acetic acid (100 mL) and HCl (72 mL, 0.86 mol). The mixture was warmed up to 120° C. and reacted under reflux for 4 h. The solvent was evaporated off. To the obtained fraction was added water (200 mL). The mixture was filtered by suction and dried to produce Intermediate h (3.2 g) in a yield of 47%.

Step Z-b 2-phenyl-3,5-dioxo-2,3,4,5-tetrahydro-1,2,4-triazine-6-carbonyl chloride (C-5)

Intermediate l (3 g, 0.015 mol) was added to thionyl chloride (10V/W, 30 mL). The mixture was warmed up under stirring to react under reflux for 6 h. The solvent was evaporated off to produce a clear yellow crystal (2.9 g) in a yield of 85%.

Step Z-c N-[3-fluoro-4-[6-methoxy-7-[3-(1-pyrrolidyl)propyloxy]quinolin]-4-oxy]phenyl]-2-(2,4-dichlorophenyl)-3,5-dicarbonyl-2,3,4,5-tetrahydro-1,2,4-triazine-6-carboxamide Example 48

Compound M-1 (0.2 g, 0.48 mmol), Compound C-5 (0.14 g, 0.58 mmol), and N,N-diisopropylethylamine (0.07 g, 0.58 mmol) were added to dried dichloromethane (10 mL). The reaction was conducted at room temperature for 10 h. After completion of the reaction, the organic layer was washed with 5% aqueous potassium carbonate solution and a saturated saline solution, dried over anhydrous magnesium sulfate, and evaporated off to produce a compound named N-[3-fluoro-4-(6-methoxy-7-(3-(1-pyrrolidyl)propyloxy)quinoline)-4-oxy)phenyl)-3,5-dicarbonyl-2-(2,4-dichlorophenyl)-2,3,4,5-tetrahydro-1,2,4-triazine-6-carboxamide (Example 48) (0.22 g) in a yield of 81.5%. ESI-MS [M+H] (m/z): 695.5.

According to the procedure of Example 48, Intermediate c with different substitutents as starting material was subjected to two reaction steps including hydrolysis and acylation to finally produce Compound C-5 with different substitutents, which was further reacted with Compound M-1 with different substitutents to produce compounds of Examples 49-52.

Example 49

N-[3-fluoro-4-[6-methoxy-7-[3-(4-morpholinyl)propyloxy]quinolin]-4-oxy]phenyl]-2-(2,4-dimethylphenyl)-3,5-dicarbonyl-2,3,4,5-tetrahydro-1,2,4-triazine-6-carboxamide ESI-MS [M+H] (m/z): 670.6.

Example 50

N-[3-fluoro-4-[6-methoxy-7-[3-(1-piperidinyl)propyloxy)quinolin]-4-oxy]phenyl]-2-(4-fluorophenyl)-3,5-dicarbonyl-2,3,4,5-tetrahydro-1,2,4-triazine-6-carboxamide ESI-MS [M+H] (m/z):658.6.

Example 51

N-[3-fluoro-4-[6-methoxy-7-[3-(4-methyl-1-piperazinyl)propyloxy]quinolin]-4-oxy]phenyl]-2-(4-bromophenyl)-3,5-dicarbonyl-2,3,4,5-tetrahydro-1,2,4-triazine-6-carboxamide ESI-MS [M+H] (m/z): 734.5.

Example 52

N-[3-fluoro-4-[6-methoxy-7-[3-(4-methyl-1-piperidinyl)propyloxy]quinolin]-4-oxy]phenyl]-2-(2-chlorophenyl)-3,5-dicarbonyl-2,3,4,5-tetrahydro-1,2,4-triazine-6-carboxamide ESI-MS [M+H] (m/z): 689.1.

Example 53

N-[3-fluoro-4-[6-methoxy-7-[2-(4-methyl-1-piperidinyl)ethoxy]quinolin-4-oxy]phenyl]-2-(3,5-difluorophenyl)-4-methyl-3,5-dioxo-2,3,4,5-tetrahydro-1,2,4-triazine-6-carboxamide ESI-MS [M+H] (m/z):690.6.

Example 54

N-[3-fluoro-4-[6-methoxy-7-[2-(4-methyl-1-piperazinyl)ethoxy]quinolin-4-oxy]phenyl]-2-(4-chlorophenyl)-4-methyl-3,5-dioxo-2,3,4,5-tetrahydro-1,2,4-triazine-6-carboxamide ESI-MS [M+H] (m/z):690.1.

Example 55

N-[3-fluoro-4-[6-methoxy-7-[2-(1-pyrrolidyl)ethoxy]quinolin-4-oxy]phenyl]-2-(4-chlorophenyl)-4-methyl-3,5-dioxo-2,3,4,5-tetrahydro-1,2,4-triazine-6-carboxamide ESI-MS [M+H] (m/z):661.0.

Example 56

N-[3-fluoro-4-[6-methoxy-7-[2-(1-piperidinyl)ethoxy]quinolin-4-oxy]phenyl]-2-(3,5-difluorophenyl)-4-methyl-3,5-dioxo-2,3,4,5-tetrahydro-1,2,4-triazine-6-carboxamide ESI-MS [M+H] (m/z):658.6.

Example 57

N-[3-fluoro-4-[6-methoxy-7-[4-(4-morpholinyl)butoxy]quinolin-4-oxy]phenyl]-2-(3-fluorophenyl)-4-methyl-3,5-dioxo-2,3,4,5-tetrahydro-1,2,4-triazine-6-carboxamide ESI-MS [M+H] (m/z):688.6.

Example 58

N-[3-fluoro-4-[6-methoxy-7-[4-(4-methyl-1-piperidinyl)butoxy]quinolin-4-oxy]phenyl]-2-(3-fluorophenyl)-4-methyl-3,5-dioxo-2,3,4,5-tetrahydro-1,2,4-triazine-6-carboxamide ESI-MS [M+H] (m/z):700.7.

Example 59

N-[3-fluoro-4-[6-methoxy-7-[4-(4-methyl-1-piperazinyl)butoxy]quinolin-4-oxy]phenyl]-2-(3-fluorophenyl)-4-methyl-3,5-dioxo-2,3,4,5-tetrahydro-1,2,4-triazine-6-carboxamide ESI-MS [M+H] (m/z):701.7.

Example 60

N-[3-fluoro-4-[6-methoxy-7-[4-(1-piperidinyl)butoxy]quinolin-4-oxy]phenyl]-2-(3-fluorophenyl)-4-methyl-3,5-dioxo-2,3,4,5-tetrahydro-1,2,4-triazine-6-carboxamide ESI-MS [M+H] (m/z):686.7.

Study on the Anti-Tumor Activities of the Present Compounds

In Vitro Anti-Tumor Cell Activities

Some compounds in the Examples were screened for the activities of inhibiting lung cancer cell H460, colon cancer cell HT-29, human gastric cancer cell MKN-45 and hepatoma carcinoma cell line SMMC-7721 in vitro.

(1) Cells were thawed and stably passaged two or three times, respectively, and then digested with trypsinase solution (0.25%) so as to be removed from the bottom of culture flasks. The digested cell solution was poured into a centrifuge tube, to which a culture media was added to stop the digestion. The centrifuge tube was centrifuged at 800r/min for 10 min, the supernatant was removed gently and then 5 mL of the culture media was added. The cells were piepetted and mixed homogeneously. 10 μL cell suspension was taken into a cell counting plate for counting, wherein the cell concentration was adjusted to $10^4$ cells/well. To each well of a 96-well plate, except for A1 well as blank control, was added 100 μL of the cell suspension. The 96-well plate was placed in an incubator and cultivated for 24 h.

(2) 50 μL dimethyl sulfoxide was used to dissolve the test samples, and then a suitable amount of the culture media was added so as to reach a final concentration of 2 mg/mL. Then the samples were diluted to 20, 4, 0.8, 0.16 and 0.032 μg/mL in a 24-well plate, respectively. There were three wells for each concentration, wherein the cell growth in the surrounding two rows and columns was significantly influenced by environments and thus only taken as blank cell wells. The 96-well plate was placed in an incubator and cultivated for 72 h.

(3) The culture media containing the compounds in the 96-well plate was removed, and the cells were washed with phosphate buffered solution (PBS) twice. To each well was added 100 μL MTT (tetrazole) (0.5 mg/mL), after placing the plate in an incubator to incubate for 4 h, the MTT solution was removed and 100 μL dimethyl sulfoxide was added. The reaction product of survival cells with MTT, i.e. formazan, was dissolved completely by oscillation on a magnetic oscillator, and then placed into a microplate reader to measure the results, and the $IC_{50}$ values of compounds could be deduced by Bliss method.

The results of the activities of the compounds for inhibiting human nonsmall-cell lung cancer cell H460, human colon cancer cell HT-29, human gastric cancer cell MKN-45 and human hepatoma carcinoma cell line SMMC-7721 are shown in Table 1.

TABLE 1

| Example | H460 $IC_{50}$(μg/mL) | HT-29 $IC_{50}$(μg/mL) | MKN-45 $IC_{50}$(μg/mL) | SMMC-7721 $IC_{50}$(μg/mL) |
|---|---|---|---|---|
| Example 1 | 0.26 | 0.12 | 0.042 | 0.18 |
| Example 2 | 0.072 | 0.18 | 0.032 | 0.20 |
| Example 3 | 0.17 | 0.14 | 0.059 | 0.10 |
| Example 4 | 0.087 | 0.13 | 0.053 | 0.071 |
| Example 5 | 0.094 | 0.12 | 0.12 | 0.15 |
| Example 6 | 0.032 | 0.06 | 0.021 | 0.11 |
| Example 7 | 0.13 | 0.27 | 0.033 | 0.21 |
| Example 8 | 0.33 | 0.28 | 0.077 | 0.42 |
| Example 9 | 0.17 | 0.21 | 0.065 | 0.09 |
| Example 10 | 0.0081 | 0.093 | 0.0065 | 0.11 |
| Example 11 | 2.1 | 1.4 | 3.3 | 2.5 |
| Example 12 | 0.12 | 0.11 | 0 | 0.74 |
| Example 13 | 0.28 | 0.19 | 0 | 0.67 |
| Example 14 | 0.15 | 0.11 | 2.1 | 0.88 |
| Example 15 | 0.18 | 0.5 | 0 | 0.79 |
| Example 16 | 0.22 | 0.3 | 0.027 | 0.34 |
| Example 17 | 0.22 | 0.3 | 0.027 | 0.19 |
| Example 18 | 0.57 | 0.3 | 0.0008 | 0.45 |
| Example 19 | 1.1 | 0.24 | 0.23 | 0.74 |
| Example 20 | 0.28 | 0.14 | 0.009 | 0.11 |
| Example 21 | 0.24 | 0.13 | 0.0002 | 0.32 |
| Example 22 | 0.26 | 0.12 | 0.006 | 0.18 |
| Example 23 | 0.57 | 0.35 | 0.0028 | 0.44 |
| Example 24 | 0.28 | 0.5 | 0.093 | 0.61 |
| Example 25 | 0.52 | 0.05 | 0.014 | 0.07 |
| Example 26 | 0.15 | 0.08 | 0.011 | 0.33 |
| Example 27 | 0.23 | 0.18 | 0.0053 | 0.58 |
| Example 28 | 0.25 | 0.31 | 0.077 | 0.44 |
| Example 29 | 0.0056 | 0.12 | 0.0009 | 0.014 |
| Example 30 | 0.18 | 0.11 | 0.043 | 0.46 |
| Example 31 | 0.14 | 0.21 | 0.066 | 0.73 |
| Example 32 | 0.09 | 0.11 | 0.005 | 0.28 |
| Example 33 | 0.15 | 0.18 | 0.09 | 0.43 |
| Example 34 | 0.028 | 0.11 | 0.013 | 0.18 |
| Example 35 | 0.12 | 0.079 | 0.005 | 0.31 |
| Example 36 | 1.7 | 0.43 | 0.21 | 2.4 |
| Example 37 | 1.7 | 0.88 | 0.12 | 2.3 |
| Example 38 | 1.4 | 0.54 | 0.62 | 1.8 |
| Example 39 | 1.4 | 0.83 | 0.19 | 2.1 |
| Example 40 | 1.0 | 0.26 | 0.05 | 3.1 |
| Example 41 | 0.8 | 1.1 | 0.06 | 1.4 |
| Example 42 | 1.1 | 0.77 | 0.11 | 0.92 |
| Example 43 | 0.65 | 0.32 | 0.07 | 1.4 |
| Example 44 | 0.99 | 0.57 | 0.13 | 2.5 |
| Example 45 | 0.34 | 0.28 | 0.05 | 1.1 |
| Example 46 | 0.8 | 0.3 | 0.1 | 1.4 |
| Example 47 | 1.1 | 0.09 | 0.4 | 3.7 | c-Met Enzyme Activity Inhibition Assay

The assay for the determination of c-Met kinase activity is based on an enzyme linked immunosorbant assay (ELISA). A compound of Formula I, 50 pM c-Met (His-tagged recombinant human Met (amino acids 974-end), expressed by baculovirus), and 5 μM ATP in an assay buffer (25 mM MOPS, pH 7.4, 5 mM MgCl2, 0.5 raM MnCl2, 100 μM sodium orthovanadate, 0.01% Triton X-100, 1 mM DTT, final DMSO concentration 1% (v/v)) were incubated on a plate coated with 0.25 mg/mL PGT at room temperature for 20 min. The reaction mixture was removed by washing and the phosphorylated polymer substrate was detected with 0.2 μg/mL phosphotyrosine specific monoclonal antibody (PY20) conjugated to horseradish peroxidase (HRP). After the addition of 1M phosphoric acid to stop the development, the chromogenic substrate (TMB) color was quantitated by spectrophotometry at 450 nm.

The data of some Example compounds for inhibiting c-Met kinase are shown in Table 2.

TABLE 2

| Example | $IC_{50}$(μg/mL) |
|---|---|
| Example 1 | 0.046 |
| Example 2 | 0.12 |
| Example 3 | 0.058 |
| Example 4 | 0.63 |
| Example 5 | 0.28 |
| Example 6 | 0.032 |
| Example 7 | 0.048 |
| Example 8 | 0.42 |
| Example 9 | 0.16 |
| Example 10 | 0.073 |
| Example 11 | 0.47 |
| Example 12 | 0.18 |
| Example 13 | 0.25 |
| Example 14 | 0.088 |
| Example 15 | 0.009 |
| Example 16 | 0.53 |
| Example 17 | 0.29 |
| Example 18 | 0.32 |
| Example 19 | 0.54 |
| Example 20 | 0.17 |
| Example 21 | 0.13 |
| Example 22 | 0.57 |
| Example 23 | 0.82 |
| Example 24 | 0.18 |
| Example 25 | 1.01 |
| Example 26 | 0.71 |
| Example 27 | 0.041 |
| Example 28 | 0.31 |
| Example 29 | 0.61 |
| Example 30 | 0.058 |
| Example 31 | 0.0063 |
| Example 32 | 0.06 |
| Example 33 | 0.27 |
| Example 34 | 0.017 |
| Example 35 | 0.03 |
| Example 36 | 1.1 |
| Example 37 | 3.7 |
| Example 38 | 2.76 |
| Example 39 | 1.8 |
| Example 40 | 5.1 |
| Example 41 | 2.7 |
| Example 42 | 1.63 |
| Example 43 | 3.8 |
| Example 44 | 6.1 |
| Example 45 | 2.72 |
| Example 46 | 8.2 |
| Example 47 | 5.92 |

As can be seen clearly from the above assay results, the claimed compounds of general formula (I) of the present invention have good activities for inhibiting c-Met kinase.

The compounds of general formula (I) according to the present invention may be administrated alone, but typically administrated in mixture with a pharmaceutically acceptable carrier. The pharmaceutically acceptable carrier is selected depending on the desired administration route and standard pharmaceutical practice. Following is a description of the preparation methods for various pharmaceutical formulations of the compounds, such as tablet, capsule, injection, aerosol, suppository, film, dripping pill, liniment for external use, and ointment to illustrate the new application of these compounds in medicine field.

Example 61

Tablet 10 g compound in the scope of the compound of claim 1 (e.g., the compound of Example 5) was mixed homogeneously with 20 g adjuvants and tabletted into 100 tablets by general compression method, 300 mg each tablet.

Example 62

Capsule 10 g compound in the scope of the compound of claim 1 (e.g., the compound of Example 3) was mixed homogeneously with 20 g adjuvants according to the requirements of pharmaceutical capsules, and filled into empty capsules, 300 mg each capsule.

Example 63

Injection 10 g compound in the scope of the compound of claim 1 (e.g., the compound of Example 1) was absorbed by activative charcoal by conventional pharmaceutical method, filtered through 0.65 μm microporous membrane and filled into a nitrogen bottle to prepare an aqueous injection preparation, 2 mL each bottle, and 100 bottles in total.

Example 64

Aerosol 10 g compound in the scope of the compound of claim 1 (e.g., the compound of Example 6) was dissolved with a suitable amount of propylene glycol, and added with distilled water and other adjuvants to get 500 mL clear solution to obtain the aerosol.

Example 65

Suppository 10 g compound in the scope of the compound of claim 1 (e.g., the compound of Example 14) was grinded and a suitable amount of glycerol was added and mixed homogeneously. Then a melt glycogelatin was added and grinded homogeneously, and the mixture was poured into a mold coated with lubricant to produce 50 suppository particles.

Example 66

Film 10 g compound in the scope of the compound of claim 1 (e.g., the compound of Example 30) was mixed and expanded with polyvinyl alcohol, pharmaceutically acceptable glycerol, water etc., and dissolved by heating. After filtration on an 80 mesh screen, the compound of Example 18 was added to the filtrate and dissolved therein by agitgation. 100 films were produced by coater machine.

Example 67

Dripping Pill 10 g compound in the scope of the compound of claim 1 (e.g., the compound of Example 17) was mixed homogeneously with 50 g matrix such as gelatin by heating and melting, and then the mixture was dropped into a liquid paraffin at low temperature. 1000 pills of dripping pill were produced.

Example 68

Liniment for External Use 10 g compound in the scope of the compound of claim 1 (e.g., the compound of Example 4) was mixed and ground with 2.5 g adjuvants such as emulsifier by conventional formulation methods, and then 200 mL water was added to prepare the liniment for external use.

Example 69

Ointment 10 g compound in the scope of the compound of claim 1 (e.g., the compound of Example 32) was ground and then mixed homogeneously with 500 g oleaginous base such as vaseline to produce the ointment.

Although the present invention has been illustrated by the specific embodiments, any modification and equivalent variation are obvious to those skilled in the art and they fall into the scope of this invention.

I claim:

1. A compound of general formula (I) or a pharmaceutically acceptable salt, solvate or prodrug thereof, wherein,
X is O, S, NH, NCH3;
Y is H, halogen;
n is an integral between 2 and 6;
R1 and R2 are identical or different, and independently and respectively selected from the group consisting of hydrogen, C1-C10alkyl, C3-C7cycloalkyl, C2-C10alkenyl and C2-C10alkynyl, which can be optionally substituted by 1-3 identical or different R4 substituents;
or R1 and R2 together with the nitrogen atom bonded thereto form 5-10 membered heterocyclyl or 5-10 membered heteroaryl, said heterocyclyl and heteroaryl optionally contain 1-4 hetero atoms selected from N, O and S besides the nitrogen atom bonded to R1 and R2, said heterocyclyl optionally comprises 1 or 2 carbon-carbon double bonds besides the nitrogen atom bonded to R1 and R2, said heterocyclyl and heteroaryl are optionally substituted by 1-3 identical or different R4 substituents;
R4 is C1-C6alkyl, hydroxy, cyano, carboxyl, an ester group;
R3 is H, C1-C4alkyl, C3-C6cycloalkyl, allyl, —CH2-Ar1;
Ar1 is phenyl, and optionally substituted by 1-3 identical or different R5 substituents;
Ar is C6-C10aryl, 5-10 membered heteroaryl, wherein said heteroaryl contains 1-3 hetero atoms selected from N, O and S, and Ar is optionally substituted by 1-3 identical or different R5 substituents;

R5 is hydroxy, halogen, nitro, amino, cyano, (C1-C6)alkyl, (C1-C6)alkenyl, (C1-C6)alkynyl, (C1-C6)alkoxyl, (C1-C6)alkyl or (C1-C6)alkoxyl optionally substituted by hydroxy, amino or halogen, mono or di[(C1-C6)alkyl] substituted amino, (C1-C6)alkylamido, a carboxyl radical which is free, salified, esterified or amidated, (C1-C6)alkylsulfinyl, sulfonyl, (C1-C6)alkoxyl, (C1-C6)alkyl, (C1-C6)alkylacyl, carbamoyl, mono or di(C1-C6alkyl) substituted carbamoyl, (C1-C3)alkylenedioxy.

2. The compound of general formula (I) according to claim 1, or a pharmaceutically acceptable salt, solvate or prodrug thereof, wherein,
   X is O, S;
   Y is halogen;
   n is an integral between 2 and 6;
   R1 and R2 are identical or different, and independently and respectively selected from the group consisting of hydrogen, C1-C6alkyl, C3-C6cycloalkyl, which can be optionally substituted by 1-3 identical or different R4 substituents;
   or R1 and R2 together with the nitrogen atom bonded thereto form 5-10 membered heterocyclyl, said heterocyclyl optionally contains 1-4 hetero atoms selected from N, O and S besides the nitrogen atom bonded to R1 and R2, said heterocyclyl optionally comprises 1 or 2 carbon-carbon double bonds or triple bonds besides the nitrogen atom bonded to R1 and R2, said heterocyclyl is optionally substituted by 1-3 identical or different R4 substituents;
   R3 is H, C1-C4alkyl, C3-C6cycloalkyl, allyl, benzyl.

3. The compound of general formula (I) according to claim 2 or a pharmaceutically acceptable salt, solvate or prodrug thereof, wherein,
   X is O;
   Y is F;
   n is an integral between 2 and 4;
   R1 and R2 together with the nitrogen atom bonded thereto form 5-6 membered heterocyclyl, said heterocyclyl optionally contains 1-3 hetero atoms selected from N, O and S besides the nitrogen atom bonded to R1 and R2, said heterocyclyl optionally comprises 1 or 2 carbon-carbon double bonds or triple bonds besides the nitrogen atom bonded to R1 and R2, said heterocyclyl is optionally substituted by 1-3 identical or different R4 substituents;
   Ar is phenyl, 5-6 membered heteroaryl, wherein said heteroaryl contains 1-3 hetero atoms selected from N, O and S, and Ar is optionally substituted by 1-3 identical or different R5 substituents;
   R3 is hydrogen, C1-C4alkyl, allyl, benzyl.

4. The compound of general formula (I) according to claim 3 or a pharmaceutically acceptable salt, solvate or prodrug thereof, wherein,
   Y is F;
   R1 and R2 together with the nitrogen atom bonded thereto form 5-6 membered saturated heterocyclyl, said saturated heterocyclyl optionally contains one hetero atom selected from N, O and S besides the nitrogen atom bonded to R1 and R2, and is optionally substituted by 1-3 identical or different R4 substituents;
   R4 is C1-C4alkyl;
   R3 is hydrogen, C1-C4alkyl;
   Ar is phenyl, pyridinyl, pyrrolyl, furyl, thienyl, and Ar is optionally substituted by 1-3 identical or different R5 substituents.

5. The compound of general formula (I) according to claim 4 or a pharmaceutically acceptable salt, solvate or prodrug thereof, wherein,
   R1 and R2 together with the nitrogen atom bonded thereto form 1-piperidinyl, 4-morpholinyl, 4-methyl-1-piperazinyl, 1-piperazinyl, 4-methyl-1-piperidinyl, 1-pyrrolidyl, 4-thiomorpholinyl;
   Ar is phenyl, and Ar is optionally substituted by 1-3 identical or different R5 substituents.

6. The compound of general formula (I) according to claim 5 or a pharmaceutically acceptable salt, solvate or prodrug thereof, wherein,
   n is 3;
   R3 is methyl, ethyl, propyl, butyl and allyl;
   R1 and R2 together with the nitrogen atom bonded thereto form 1-piperidinyl, 4-morpholinyl, 4-methyl-1-piperazinyl, 4-methyl-1-piperidinyl, 1-pyrrolidyl.

7. The compound of general formula (I) according to claim 6 or a pharmaceutically acceptable salt, solvate or prodrug thereof, wherein,
   R3 is methyl.

8. The compound of general formula (I) according to claim 7 or a pharmaceutically acceptable salt, solvate or prodrug thereof, wherein,
   R5 is halogen, (C1-C4)alkyl, (C1-C4)alkoxyl, (C1-C4)alkyl or (C1-C4)alkoxyl optionally substituted by halogen, mono or di(C1-C6alkyl) substituted amino, (C1-C4)alkoxyl(C1-C4)alkyl, (C1-C6)alkylacyl, carbamoyl, mono or di(C1-C6alkyl) substituted carbamoyl, (C1-C3)alkylenedioxy.

9. The compound of general formula (I) according to claim 8 or a pharmaceutically acceptable salt, solvate or prodrug thereof, wherein,
   R5 is halogen, methyl, ethyl, methoxy, ethoxy, trifluoromethyl and trifluoromethoxy.

10. The compound of general formula (I) according to claim 9 or a pharmaceutically acceptable salt, solvate or prodrug thereof, wherein,
    R5 is fluoro, chloro, trifluoromethyl and methyl.

11. The following compound of general formula (I) according to claim 1 or a pharmaceutically acceptable salt, solvate or prodrug thereof:
    N-[3-fluoro-4-[6-methoxy-7-[3-(4-morpholinyl)propyloxy]quinolin-4-oxy]phenyl]-2-phenyl-4-methyl-3,5-dioxo-2,3,4,5-tetrahydro-1,2,4-triazine-6-carboxamide;
    N-[3-fluoro-4-[6-methoxy-7-[3-(4-morpholinyl)propyloxy]quinolin-4-oxy]phenyl]-2-phenyl-4-methyl-3,5-dioxo-2,3,4,5-tetrahydro-1,2,4-triazine-6-carboxamide;
    N-[3-fluoro-4-[6-methoxy-7-[3-(1-piperidinyl)propyloxy]quinolin-4-oxy]phenyl]-2-phenyl-4-methyl-3,5-dioxo-2,3,4,5-tetrahydro-1,2,4-triazine-6-carboxamide;
    N-[3-fluoro-4-[6-methoxy-7-[3-(1-pyrrolidyl)propyloxy]quinolin-4-oxy]phenyl]-2-phenyl-4-methyl-3,5-dioxo-2,3,4,5-tetrahydro-1,2,4-triazine-6-carboxamide;
    N-[3-fluoro-4-[6-methoxy-7-[3-(4-methyl-1-piperazinyl)propyloxy]quinolin-4-oxy]phenyl]-2-phenyl-4-methyl-3,5-dioxo-2,3,4,5-tetrahydro-1,2,4-triazine-6-carboxamide;
    N-[3-fluoro-4-[6-methoxy-7-[3-(4-morpholinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-4-methyl-3,5-dicarbonyl-2-(3-trifluoromethylphenyl)-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(4-morpholinyl)propyloxy)quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(3-fluorophenyl)-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(morpholin-1-yl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperidinyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-phenyl-4-butyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-phenyl-4-butyl-3,5-dioxo-2,3,4,5-tetrahydro-1,2,4-triazine-6-carboxamide;

N-[3-fluoro-4-[7-methoxy-6-[3-(4-methyl-1-piperazinyl)propyloxy]quinolin-4-oxy]phenyl]-2-phenyl-4-butyl-3,5-dioxo-2,3,4,5-tetrahydro-1,2,4-triazine-6-carboxamide;

N-[3-fluoro-4-[7-methoxy-6-[3-(4-methyl-1-piperidinyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(4-methyl-1-piperazinyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(4-methyl-1-piperazinyl)propyloxy]quinolin-4-oxy]phenyl]-2-(4-chlorophenyl)-4-allyl-3,5-dioxo-2,3,4,5-tetrahydro-1,2,4-triazine-6-carboxamide;

N-[3-fluoro-4-[7-methoxy-6-[3-(4-methyl-1-piperidinyl)propyloxy]quinolin-4-oxy]phenyl]-2-(4-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-trifluoromethylphenyl)-4-allyl-3,5-dioxo-2,3,4,5-tetrahydro-1,2,4-triazine-6-carboxamide;

N-[3-fluoro-4-[7-methoxy-6-[3-(1-piperidinyl)propyloxy]quinolin-4-oxy]phenyl]-2-(2-trifluoromethylphenyl)-4-allyl-3,5-dioxo-2,3,4,5-tetrahydro-1,2,4-triazine-6-carboxamide;

N-[3-fluoro-4-[7-methoxy-6-[3-(1-piperidinyl)propyloxy]quinolin-4-oxy]phenyl]-2-phenyl-4-allyl-3,5-dioxo-2,3,4,5-tetrahydro-1,2,4-triazine-6-carboxamide;

N-[3-fluoro-4-[7-methoxy-6-[3-(4-methyl-1-piperidinyl)propyloxy]quinolin-4-oxy]phenyl]-2-(4-chlorophenyl)-4-allyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-(2-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(3-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-methylphenyl)-4-allyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(4-morpholinyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(1-piperidinyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin]-4-oxy]phenyl]-2-(4-chlorophenyl)-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(4-morpholinyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(1-piperidinyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin]-4-oxy]phenyl]-2-(4-fluorophenyl)-3,5-dioxo-2,3,4,5-tetrahydro-1,2,4-triazine-6-carboxamide;

N-[3-fluoro-4-[6-methoxy-7-[3-(1-piperidinyl)propyloxy]quinolin]-4-oxy]phenyl]-2-(3-trifluoromethylphenyl)-4-benzyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin]-4-oxy]phenyl]-2-(3-trifluoromethylphenyl)-4-benzyl-3,5-dioxo-2,3,4,5-tetrahydro-1,2,4-triazine-6-carboxamide.

12. The following compound of general formula (I) according to claim 1 or a pharmaceutically acceptable salt, solvate or prodrug thereof:

N-[3-fluoro-4-[6-methoxy-7-[3-(4-morpholinyl)propyloxy]quinolin-4-oxy]phenyl]-2-phenyl-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-fluorophenyl)-4-methyl-3,5-dioxo-2,3,4,5-tetrahydro-1,2,4-triazine-6-carboxamide;

N-[3-fluoro-4-[6-methoxy-7-[3-(4-methyl-1-piperazinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3,4-difluorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(3-trifluoromethylphenyl)-4-methyl-3,5-dicarbonyl-2,3,4,5-tetrahydro-1,2,4-triazine-6-carboxamide;

N-[3-fluoro-4-[6-methoxy-7-[3-(4-morpholinyl)propyloxy]quinolin-4-oxy]phenyl]-2-(4-chlorophenyl)-4-methyl-3,5-dioxo-2,3,4,5-tetrahydro-1,2,4-triazine-6-carboxamide;

N-[3-fluoro-4-[6-methoxy-7-[3-(1-pyrrolidyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[6-methoxy-7-[3-(1-piperidinyl)propyloxy]quinolin-4-oxy]phenyl]-2-(4-methylphenyl)-4-methyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-phenyl-4-butyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-(2-trifluoromethylphenyl)-4-butyl-3,5-dioxo-2,3,4,5-tetrahydro-1,2,4-triazine-6-carboxamide;

N-[3-fluoro-4-[7-methoxy-6-[3-(4-methyl-1-piperazinyl)propyloxy]quinolin-4-oxy]phenyl]-2-(4-chlorophenyl)-4-allyl-3,5-dioxo-2,3,4,5-tetrahydro-1,2,4-triazine-6-carboxamide;

N-[3-fluoro-4-[7-methoxy-6-[3-(4-methyl-1-piperidinyl)propyloxy]quinolin-4-oxy]phenyl]-2-(4-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-trifluoromethylphenyl)-4-allyl-3,5-dioxo-2,3,4,5-tetrahydro-1,2,4-triazine-6-carboxamide;

N-[3-fluoro-4-[7-methoxy-6-[3-(1-pyrrolidyl)propyloxy]quinolin-4-oxy]phenyl]-2-(2-fluorophenyl)-4-allyl-3,5-dioxo-2,3,4,5-tetrahydro-1,2,4-triazine-6-carboxamide;

N-[3-fluoro-4-[7-methoxy-6-[3-(4-morpholinyl)propyloxy]quinolin-4-oxy]phenyl]-2-(2-methylphenyl)-4-allyl-3,5-dioxo-2,3,4,5-tetrahydro-1,2,4-triazine-6-carboxamide.

13. A pharmaceutical composition, containing a compound according to claim 1 or a pharmaceutically acceptable salt, hydrate, solvate or prodrug thereof as active component and a pharmaceutically acceptable excipient.

* * * * *